(12) United States Patent
Wabl et al.

(10) Patent No.: US 11,946,063 B2
(45) Date of Patent: Apr. 2, 2024

(54) LONG GERMLINE DH GENES AND LONG HCDR3 ANTIBODIES

(71) Applicant: TRIANNI, INC., Wilmington, DE (US)

(72) Inventors: Matthias Wabl, San Francisco, CA (US); Werner Mueller, Cologne (DE); Peter Burrows, Birmingham, AL (US); Gloria Esposito, Vienna (AT); Bao Duong, Pacifica, CA (US)

(73) Assignee: TRIANNI, INC., Wilmington, DE (US)

( * ) Notice: Subject to any disclaimer, the term of this patent is extended or adjusted under 35 U.S.C. 154(b) by 0 days.

(21) Appl. No.: 16/165,018

(22) Filed: Oct. 19, 2018

(65) Prior Publication Data

US 2019/0127757 A1  May 2, 2019

(30) Foreign Application Priority Data

Oct. 27, 2017 (EP) ..................... 17198800

(51) Int. Cl.
| | |
|---|---|
| C12N 15/85 | (2006.01) |
| A01K 67/027 | (2006.01) |
| A01K 67/0278 | (2024.01) |
| C07K 16/18 | (2006.01) |
| C12N 5/074 | (2010.01) |
| C12N 15/10 | (2006.01) |
| C12N 15/62 | (2006.01) |
| C40B 40/10 | (2006.01) |

(52) U.S. Cl.
CPC ...... *C12N 15/8509* (2013.01); *A01K 67/0278* (2013.01); *C07K 16/18* (2013.01); *C12N 5/0696* (2013.01); *C12N 15/1072* (2013.01); *C12N 15/62* (2013.01); *C40B 40/10* (2013.01); *A01K 2207/15* (2013.01); *A01K 2217/054* (2013.01); *A01K 2217/072* (2013.01); *A01K 2227/105* (2013.01); *A01K 2267/01* (2013.01); *A01K 2267/03* (2013.01); *C12N 2015/8518* (2013.01); *C12N 2015/8527* (2013.01)

(58) Field of Classification Search
CPC .......... C12N 5/0696; C12N 2015/8527; C12N 15/62; C12N 2015/8518; C12N 15/1072; C12N 15/8509; A01K 2267/01; A01K 2217/072; A01K 67/0278; A01K 2227/105; A01K 2207/15; A01K 2217/054; A01K 2267/03; C40B 40/10; C07K 16/18
See application file for complete search history.

(56) References Cited

U.S. PATENT DOCUMENTS

| | | | |
|---|---|---|---|
| 5,591,669 A | 1/1997 | Krimpenfort et al. | |
| 5,593,598 A | 1/1997 | McGinness et al. | |
| 5,612,205 A | 3/1997 | Kay et al. | |
| 5,661,016 A | 8/1997 | Lonberg et al. | |
| 5,789,650 A | 8/1998 | Lonberg et al. | |
| 5,814,318 A | 9/1998 | Lonberg et al. | |
| 5,874,299 A | 2/1999 | Lonberg et al. | |
| 5,887,397 A | 3/1999 | Repasky | |
| 6,023,010 A | 2/2000 | Krimpenfort et al. | |
| 6,091,001 A | 7/2000 | Jakobovits et al. | |
| 6,130,364 A | 7/2000 | Jakobovits et al. | |
| 6,162,963 A | 12/2000 | Kucherlapati et al. | |
| 6,570,061 B1 | 5/2003 | Rajewsky et al. | |
| 6,596,541 B2 | 7/2003 | Murphy et al. | |
| 6,673,986 B1 | 1/2004 | Kucherlapati et al. | |
| 7,041,871 B1 | 5/2006 | Lonberg et al. | |
| 7,064,244 B2 | 6/2006 | Jakobovits et al. | |
| 7,145,056 B2 | 12/2006 | Jakobovits et al. | |
| 9,644,021 B2 * | 5/2017 | Wang ................. C07K 14/64 | |
| 2013/0219535 A1 * | 8/2013 | Wabl ................ A01K 67/027 | |
| | | | 800/18 |

FOREIGN PATENT DOCUMENTS

| | | |
|---|---|---|
| WO | 2011/158009 A1 | 12/2011 |
| WO | 2013/041844 A2 | 3/2013 |
| WO | 2017/035252 A1 | 3/2017 |
| WO | 2021/003152 A1 | 1/2021 |

OTHER PUBLICATIONS

Brevini et al Theriogenology, vol. 74, pp. 544-550 (Year: 2010).*
Paris et al. Theriogenology, vol. 74, pp. 516-524 (Year: 2010).*
Munoz et al. Stem Cell Rev. and Rep., vol. 5, 6-9 (Year: 2009).*
Ezashi et al Annu. Rev. Anim. Biosci. 4:223-53 (Year: 2016).*
Hong et al. Stem Cells and Development, vol. 21(9), pp. 1571-1586 (Year: 2012).*
Tong et al. Nature, vol. 467(7312), pp. 211-213 (Year: 2010).*
Liu et al Developmental Dynamics, 209, 85-91 (Year: 1997).*
Ivics et al. Nature Protocols, vol. 9(4), pp. 810-827 (Year: 2014).*
West et al., J. Equine Vet. Sci., vol. 41, pp. 1-12 (Year: 2016).*
Meng et al. J. Animal Sci. and Biotech, pp. 1-7 (Year: 2015).*
Patil et al., Indian Journal of Public Health research & Development, vol. 2, No. 1, 106-109 (Year: 2011).*
Khodarovich et al., Applied Biochemistry and Microbiology, vol. 49, No. 9, 711-722 (Year: 2013).*
Maksimenko et al Acta Naturae, vol. 5, No. 1, 33-46 (Year: 2013).*
Yang et al., PNAS, 113(41), E6209-E6218, 1-10 (Year: 2016).*
Guo et al. Cell Research, vol. 25, 767-768 (Year: 2015).*

(Continued)

*Primary Examiner* — Anoop K Singh
(74) *Attorney, Agent, or Firm* — MEDLER FERRO WOODHOUSE & MILLS PLLC

(57) ABSTRACT

The invention relates to a long DH (LDH) cassette comprising a recombinant DH construct comprising at least two DH gene segments encoding at least 10 amino acids of the HCDR3 amino acid sequence, wherein at least one of the DH gene segments is a heterologous DH gene segment; an immunoglobulin heavy chain locus and a transgenic non-human animal comprising the same; and their use in producing an immunoglobulin library with long HCDR3 regions.

7 Claims, 9 Drawing Sheets

Figure 1:
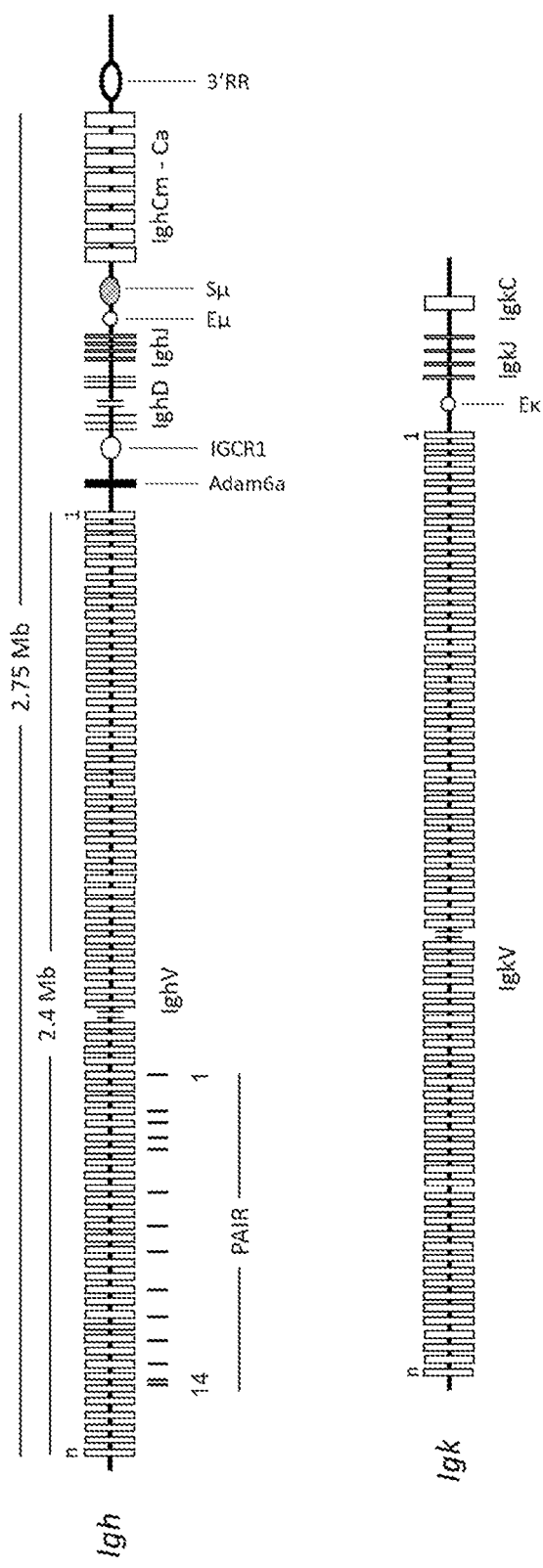

Specification includes a Sequence Listing.

(56) References Cited

OTHER PUBLICATIONS

Hsu et al Nat Biotechnology. Sep.;31(9):827-32 (Year: 2013).*
Lee et al., Drug Discovery Today: Disease Models, vol. 20, 13-20 (Year: 2016).*
Parng, The Journal of Immunology, 157: 5478-5486 (Year: 1996).*
Kaushik, Veterinary Immunology and immunopathology 87 347-350 (Year: 2002).*
Zhang et al ACS Chem Biol. Oct. 18; 8(10): 2117-2121 (Year: 2013).*
Liu et al PNAS, 1356-1361 (Year: 2015).*
Wang et al Cell, 153, 6, 1379-1393 (Year: 2013).*
Yu et al Frontiers in Immunology, 5, 1-8 (Year: 2014).*
Rosner et al Immunology 103:179-187 (Year: 2001).*
Tuaillon et al Eur J Immunol 30:2998-3005 (Year: 2000).*
Zemlin et al J Mol Biol 334:733-749 (Year: 2003).*
Stamatopoulos et al Leukemia 13, 601-604 (Year: 1999).*
Briney et al Immunology 137:56-64 (Year: 2012).*
Wang et al Cell, 153, 1379-1393 (Year: 2013).*
Zemlin et al J Immunol 181:8416-8424 (Year: 2008).*
Murphy and Weaver, Janeway's immunobiology, 9th edition The Generation of Lymphocyte Antigen Receptors, chapter 5, pp. 2173-2183 (Year: 2016).*
Araki et al., "Targeted integration of DNA using mutant lox sites in embryonic stem cells," Nucleic Acids Research 25(4):868-872 (1997).
Baer et al., "Coping with kinetic and thermodynamic barriers: RMCE, an efficient strategy for the targeted integration of transgenes," Curr Opin Biotechnol. 12:473-480 (2001).
Bassing et al., "The Mechanism and Regulation of Chromosomal V(D)J Recombination," Cell 109:S45-S55 (2002).
Bole et al., "Posttranslational Association of Immunoglobulin Heavy Chain Binding Protein with Nascent Heavy Chains in Nonsecreting and Secreting Hybridomas," J. Cell Biol. 102:1558-1566 (1986).
Briney et al., "Secondary mechanisms of diversification in the human antibody repertoire," Frontiers in Immunology 4(42):1-7 (2013).
Briney et al., "Frequency and genetic characterization of V(DD)J recombinants in the human peripheral blood antibody repertoire," Immunology 137:56-64 (2012).
Briney et al., "Human Peripheral Blood Antibodies with Long HCDR3s Are Established Primarily at Original Recombination Using a Limited Subset of Germline Genes," PloS One 7(5):e36750-e36750 (2012).
Brodeur et al., "Mouse-Human Myeloma Partners for the Production of Heterohybridomas," Monoclonal Antibody Production Techniques and Applications, (Marcel Dekker, Inc., New York) pp. 51-63 (1987).
Chenna et al., "Multiple sequence alignment with the Clustal series of programs," Nucleic Acids Research 31(13):3497-3500 (2003).
Vree et al., "Targeted sequencing by proximity ligation for comprehensive variant detection and local haplotyping," Nature Biotechnology 32(10):1019-1025 (2014).
Easterhoff et al., "Boosting of HIV envelope CD4 binding site antibodies with long variable heavy third complementarity determining region in the randomized double blind RV305 HIV-1 vaccine trial," PLoS Pathogens 13(2): e1006182 (2017).
Haas et al., "Immunoglobulin heavy chain binding protein," Nature 306:387-389 (1983).
He et al., "Knock-in of large reporter genes in human cells via CRISPR/Cas9-induced homology-dependent and independent DNA repair," Nucleic Acids Research 44(9):e85 (2016).
Hoess et al., "The role of the loxP spacer region in P1 site-specific recombination," Nucleic Acids Research 14(5):2287-2300 (1986).
Köhler et al., "Continuous cultures of fused cells secreting antibody of predefined specificity," Nature 256:495-497 (1975).
Kozbor et al., "A Human Hybrid Myeloma for Production of Human Monoclonal Antibodies," The Journal of Immunology 133(6):3001-3005 (1984).
Kunkel et al., "Rapid and efficient site-specific mutagenesis without phenotypic selection," Proc. Natl. Acad. Sci. 82(2):488-492 (1985).
Langer et al., "A genetic screen identifies novel non-compatible loxP sites," Nucleic Acids Research 30(14):3067-3077 (2002).
Lee et al., "Role of nucleotide sequences of loxP spacer region in Cre-mediated recombination," Gene 216:55-65 (1998).
Lee et al., "Strand Selection by the Tyrosine Recombinases," Progress in Nucleic Acid Research and Molecular Biology 80:1-42 (2005).
Lefranc et al., "Role of nucleotide sequences of loxP spacer region in Cre-mediated recombination," Nucleic Acids Research 27(1):209-212 (1999).
LeiYu et al., "Immunologic basis for long HCDR3s in broadly neutralizing antibodies against HIV-1," Frontiers in Immunology 5(250):1-8 (2014).
Liu et al., "Functional human antibody CDR fusions as long-acting therapeutic endocrine agonists," PNAS 112(5):1356-1361 (2015).
Muyldermans et al., "Distinct antibody species: structural differences creating therapeutic opportunities," Current Opinion in Immunology 40:7-13 (2016).
Eduardo A. Padlan, "Anatomy of the Antibody Molecule," Molecular Immunology 31(3):169-217 (1994).
Sela-Culang et al., "The structural basis of antibody-antigen recognition," Frontiers in Immunology 4(302):1-13 (2013).
Tonegawa et al., "Somatic generation of antibody diversity," Nature 302:575-581 (1983).
Wang et al., "Reshaping Antibody Diversity," Cell 153(6):1379-1393 (2013).
Weiner et al., "Site-directed mutagenesis of double-stranded DNA by the polymerase chain reaction," Gene 151(1-2):119-123 (1994).
Zhang et al., "An Antibody CDR3-Erythopeietin Fusion Protein," ACS Chemical Biology 8(10):2117-2121 (2013).
Extended European Search Report issued in European Application No. 1719880.9, dated Jan. 18, 2018.
Communication pursuant to Article 94(3) EPC dated Apr. 9, 2020 in corresponding European Patent Application No. 17 198 800.9.
Communication pursuant to Rule 114(2) EPC dated Jun. 15, 2020 in corresponding European Patent Application No. 17 198 800.9.
Tuaillon, Nadine et al., "VHD rearrangements in human immunoglobulin heavy chain minilocus transgenic mice", European Journal of Immunology, Nov. 29, 2000, vol. 30, Issue 10, pp. 2998-3005.
Zemlin, Michael et al., "Expressed Murine and Human CDR-H3 Intervals of Equal Length Exhibit Distinct Repertoires that Differ in their Amino Acid Composition and Predicted Range of Structures", Journal of Molecular Biology, Dec. 5, 2003, vol. 334, Issue 4, pp. 733-749.
Communication pursuant to Rule 114(2) EPC dated Feb. 19, 2021 in corresponding European Application No. 17 198 800.9.
Murphy and Weaver, "Janeway's Immunobiology," Ninth Edition 2016, Garland Science Chapter 5.
Lefranc and Lefranc, The Immunoglobulin Facts Book. Academic Press, Section II, Part 2, pp. 98-102 (2001).

* cited by examiner

Long Germline DH (*LDH*) Gene Cassette

Fig. 9

Table 1

SEQ ID NO:6 IGHDS2
actactgtgcaccagAGTTGTCCTGATGGTTATAGTTATGGTTATGGTTGTGGTTATGGT
GGTTATAGTAGTTATAGTTATAGTTATACTTACGAATATAC
SEQ ID NO:7 DH3.1 (lower case indicates mutated residues)
AGACTATCGgGAgGATGGTTACTGCTACACCCACAGgGACTCAGGCCCgGACATAcAGTCgGACCCGCACAC
AGGTGTGGAGCTGGCCAATGCATCCCCAGGGGCACTGGGCTCCCAAGCA

Table 2 (lower case indicates mutated residues)

SEQ ID NO:8 D1-1, 1-7, 1-14
GGTACAACTGGAACGACGGTATAtCTGGAACTACGGTATAtCCGGAACCAC
SEQ ID NO:9 D1-20, 1-26, 7-27
GGTATAtCTGGAACGACGGTATAtGGGAGCTACTACCTAtCTGGGGAC
SEQ ID NO:10 D1-26, 2-2
GGTATAtTGGGAGCTACTACAGGATATTGTAtTAtTACCAGCTGCTATGCCC
SEQ ID NO:11 D2-8, 2-15
AGGATATTGTACTAtTGGTGTATGCTATACCAGGATATTGTAtTGGTGGTAtCTGCTACTCC
SEQ ID NO:12 D2-21*02, 3-3
agcatattgtggtggggactgctattcCGTATTACGATTTTTGGAGTGGTTATTATACC
SEQ ID NO:13 D3-16, 3-22
GTATTAcGATTACGTTTGGGGGAGTTATGCTTATACCGTATTACTAgGATAtTAtTGGTTATTACTAC
SEQ ID NO:14 D4-4, 4-17, 4-23
gGACTACAGTAtCTACgGACTACGGgGACTACgGACTACGGTGGTAtCTCC
SEQ ID NO:15 D5-5, 5-12, 5-18
GTGGATACAGCTATGGTTACGTGGATATAtTGGCTACGATTACGTGGATACAGCTATGGTTAC
SEQ ID NO:16 D5-24, 6-6, 6-13, 6-25
GAGTATAtCAGCTCGTCCGGGTATAtCAGCAGCTGGTACGGGTATAtCAGCGGCTAC

Table 3 (lower case indicates mutated residues)
SEQ ID NO:17 D2-2
AGGATATTGTAtTAtTACCAGCTGCTATGCC
SEQ ID NO:18 D2-15
AGGATATTGTAtTGGTGGTAtCTGCTACTCC
SEQ ID NO:19 D3-3*02
GTATTAtCATTTTTGGAGTGGTTATTATACC
SEQ ID NO:20 D3-16*02
GTATTATGtTACGTTTGGGGGAGTTATCGTTATACC

Fig. 9 continued

Table 4

```
     SEQ ID NO:21 AJ249635
TGCATTACCTCGGTTTCGGCACTTACTATAGGG
     SEQ ID NO:22 AJ010445
GTCGCTGGCGTAGACTGGGAGTTAGTTCTTCTGC
     SEQ ID NO:23 AF062262
TGGCGGACTACGGTGACTACCCGGGAG
     SEQ ID NO:24 AF062179
TGGGGCACCGAATCTAGGTGTAGTGGTGGTAGCTGCTACTCGTC
     SEQ ID NO:25 AB374348
AAGATATCATGACAGTAGTGGTTTTTTGCGGGACTACTACTAT
     SEQ ID NO:26 AB363174
AAATTACCATGATAGTAGTGGCAATTTCTCTA
     SEQ ID NO:27 AB363161
TTTAAGGAGGCGAGGTGGCTCCGGTTATTACTCTGGTCCGGGGAGTTATTATACCAACTATCGGATGAAT
     SEQ ID NO:28 AB363155
GGGGTCGGTAGCAGCAGCTGGCGCGCACGCAGGTC
     SEQ ID NO:29 AB363151
TTCCGCCCGCCCCCCGTCGGGGCAGTGGCTGGTATGG
     SEQ ID NO:30 AB363142
GACCCCGTATTGCTCGCAGTCCGTGGCGTTTAGCAGCAGCTGGA
     SEQ ID NO:31 U32203
GGGGGAGCGTGGTGGTAGCTGCTACCCCGGGG
     SEQ ID NO: 32 JQ304251
AAGAAACGTATTACGATTTTTGGAGTGGTTAC
     SEQ ID NO:33 EU099152
AGGCCGGATTCCTTGGAGTGGCCACCCCCTGGGGGACCC
     SEQ ID NO:34 EU099082
ATGGGGGTCGATCCCCTGGTCGGGGAGTAGTACCAGCTGCTATGGGAATTGTATGGGG
     SEQ ID NO:35 E00167
AAAGTGACCCTTTTTGGAGTGATTATTATAACTTTGACTACTCGTACACTT
     SEQ ID NO:36 AY393653
TGTCCTATCGTTCGGGGAATTATTATGACGATTTTGGTTTCTCACCGGAGTTTTACTTTTACTC
     SEQ ID NO:37 GU272045
GCTGGTGGGCCCGACTACCGTAATGGGTACAACTATTACGATTTCTATGATGGTTATTATA
     SEQ ID NO:38 GU272043.1
GGCTGGTGGGCCAATCTGGCATGACGACGTCAAATATTACGATTTTAATGACGGC
     SEQ ID NO:39 AY539808
TTTGGCCCCGACTGGGAAGACGGTGATTCCTATGATGGTAGTGGCCGGGGGTT
     SEQ ID NO:40 JX206996.1
GCATATGTCGATGCAGCAGGTGGTTTCGGCGGGGTGGGAACGAGCAGACCTTGTGGGC
```

LONG GERMLINE DH GENES AND LONG HCDR3 ANTIBODIES

FIELD OF THE INVENTION

The invention relates to long heavy chain complementarity determining region 3 (HCDR3) antibodies, and methods of producing the same in vitro and in vivo.

BACKGROUND OF THE INVENTION

Antibodies have emerged as important biological pharmaceuticals because they (i) exhibit exquisite binding properties that can target antigens of diverse molecular forms, (ii) are physiological molecules with desirable pharmacokinetics that make them well tolerated in treated humans and animals, and (iii) are associated with powerful immunological properties that naturally ward off infectious agents. Furthermore, established technologies exist for the rapid isolation of antibodies from laboratory animals, which can readily mount a specific antibody response against virtually any foreign substance not present natively in the body.

In their most elemental form, antibodies are composed of two identical heavy (H) chains that are each paired with an identical light (L) chain. The N-termini of both H and L chains consist of a variable domain (VH and VL, respectively) that together provide the paired H-L chains with a unique antigen-binding specificity. The exons that encode the antibody VH and VL domains do not exist in the germ-line DNA. Instead, each VH exon is generated by the recombination of randomly selected V, D, and J gene segments present in the H chain locus (Igh); likewise, individual VL exons are produced by the chromosomal rearrangements of randomly selected V and J gene segments in a light chain locus (Igl) (see schematic of the mouse Igh locus and Igl kappa locus (Igk) in FIG. 1) (Tonegawa, Nature, 302:575-81, 1983; Bassing, et al., Cell, 109 Suppl:S45, 2002). The mouse genome contains two alleles that can express the H chain (one allele from each parent), two alleles that can express the kappa (κ) L chain, and two alleles that can express the lambda (λ) L chain. There are multiple V, D, and J gene segments at the H chain locus as well as multiple V and J genes at both L chain loci. Downstream of the J genes at each immunoglobulin (Ig) locus exist one or more genes that encode the constant region of the antibody. In the heavy chain locus, exons for the expression of different antibody classes (isotypes) also exist. In mice, the encoded isotypes are IgM, IgD, IgG1, IgG2a/c, IgG2b, IgG3, IgE, and IgA; in humans they are IgM, IgD, IgG1, IgG2, IgG3, IgG4, IgE, IgA1 and IgA2.

During B cell development, gene rearrangements occur first on one of the two homologous chromosomes that contain the H chain V, D, and J gene segments. In pre-B cells, the resultant VH exon is then spliced at the RNA level to the exons that encode the constant region of the µH chain. Most of the pH chain synthesized by pre-B cells is retained in the endoplasmic reticulum (ER) and eventually degraded due to the non-covalent interaction between the µH chain partially unfolded CH1 domain and the resident ER chaperone BiP (Haas and Wabl, Nature, 306:387-9, 1983; Bole et al., J Cell Biol. 102:1558, 1986). However, a small fraction of the µ chains associates with the surrogate light chain complex, composed of invariant λ5 and VpreB proteins, displacing BiP and allowing the µH chain/λ5/VpreB complex, together with Igα/β signaling molecules, to exit the ER as the preB Cell Receptor (preBCR) and traffic through the secretory pathway to the plasma membrane.

Subsequently, VJ rearrangements occur on one L chain allele at a time until a functional L chain is produced, after which the L chain polypeptides can completely displace BiP and associate with the µH chains to form a fully functional B cell receptor for antigen (BCR) expressed on the surface of the immature B cell. Upon migration to secondary lymphoid organs, the now mature B cells can respond to cognate antigen and differentiate into antibody-secreting plasmacytes and memory B cells. Particularly when they receive T cell help, the B cells can also undergo isotype switching, which changes the antibody isotype from IgM to IgG, IgA or IgE, as well as somatic hypermutation, which can change the amino acid sequence of the VH and VL exons. Although these mutations are introduced randomly into the VH and VL exons, B cells with higher affinity for the immunizing antigen are able to take up more of the antigen, process it and present it to T follicular helper cells and thus are preferentially activated compared to B cells with low or no affinity for the immunizing antigen. As a result, the somatic mutations become enriched in the complementarity determining regions (CDR) 1, 2 and 3, since these are the regions of the VH and VL domains that interact with the antigen.

Among the VH and VL CDRs, HCDR3 is the most diverse since it is formed de novo during VDJ rearrangement, encoded by the 3' end of the VH, the DH, and the 5' end of the JH. Moreover, insertion of non-templated nucleotides (N-sequences) added during the rearrangement process to give VH-N-DH-N-JH, combined with exonuclease nibbling to remove nucleotides from the rearranging gene segments increases diversity even further. Structurally, HCDR3 lies at the center of the antigen binding site and because of its diversity in length and amino acid sequence composition, HCDR3 is often considered the most important CDR for antigen binding (Sela-Culang, et al., Front. Immunol. 4:302, 2013; Padlan, Mol. Immunol. 31:169, 1994). The average HCDR3 length differs among species, in humans it is 15.2±4.1 amino acids, but it is shorter in mice (11.5±2.7). At the other extreme, a subset of bovine antibodies have the longest known HCDR3s ranging from 50 to 61 amino acids.

In a typical mouse or human antibody, HCDR3, together with the other CDRs that surround it, forms a relatively flat surface to interact with antigen. This structure imposes constraints on the ability of the antibody to interact with buried or otherwise inaccessible epitopes on antigens, in particular large antigens such as viruses. In the bovine "ultralong HCDR3" antibodies the HCDR3 forms a protruding stalk that supports a disulfide-rich knob that mediates antigen binding (Wang, et al., Cell 153:1379, 2013). Human antibodies with protruding long HCDR3s, although not as long as the ultralong bovine antibodies and lacking the unique knob structure of the bovine antibodies, have also been described and shown to be important for neutralization of HIV, influenza viruses and other antigens.

Antibodies with long HCDR3s are attractive as therapeutics since the antigen-binding portion of the molecule can recognize epitopes within pockets of protein structure, which include enzyme active sites and epitopes on viruses and G-coupled protein receptors that are otherwise inaccessible to conventional Abs. Numerous studies have shown that antibodies with longer than average HCDR3s neutralize a wide variety of pathogens such as HIV, malaria and African trypanosomes, as well as matrix metalloproteinases involved in cancer metastases. However, there are natural constraints on both HCDR3 length and germline diversity of this region.

The HCDR3 length in experimental animals typically used to generate clinically useful monoclonal antibodies, most often mice but sometimes rats or rabbits, is limited by several mechanisms. First, the length of the germline DH gene segments, which contribute significantly to HCDR3 length, is relatively short, averaging, e.g., 33 nt in mice. There are also certain "rules" that govern the order of Ig HC gene segment rearrangement so that usually D>J rearrangement occurs first and is followed by V>DJ rearrangement to form the complete VDJ exon. Other types of rearrangements, e.g., V(DD)J or V(DDD)J, which would greatly increase HCDR3 length, are rare because of the so-called 12/23 bp rule. Rearrangement of Ig gene segments is governed by DNA recombination signal sequences (RSS), which are recognized and cleaved by Recombinase Activating Genes (RAG) 1 and 2 proteins. The RSS contain either a 12 or 23 bp spacer sequence and the 12/23 bp rule is based on the finding that a gene segment will nearly always recombine with another gene segment having a different spacer length, i.e., a 12 bp with a 23 bp. Since the D gene segment is flanked on both sides by a 12 bp RSS, it usually recombines only with J or V gene segments, which have 23 bp RSS at their 5' and 3' ends, respectively, and not with other D gene segments. However, the 12/23 bp rule is not inviolate, e.g., Briney et al. (Immunology, 137:56-64, 2012) described the presence of B cells with heavy chain V(DD)J recombinants in the human peripheral blood antibody repertoire at a low frequency (~1 in 800 blood B cells).

Briney et al. described high throughput sequencing of human peripheral blood B cells to show that long HCDR3s (≥24 amino acids) and very long HCDR3s (≥28 amino acids) are present at low frequency (3.5%) in the naïve B cell repertoire, although it declined in the memory B cell subsets (PLoS ONE, 7:e36750, 2012), and thus such B cells can survive central tolerance mechanisms in the bone marrow and participate in immune responses.

Briney et al. (Frontiers in Immunology 2013, doi: 10.3389/fimmu.2013.00042) described the rarely occurring secondary mechanisms for diversification of the human antibody repertoire, which include V(DD)J recombination (or D-D fusion) and somatic hypermutation (SHM)-associated insertions and deletions.

Yong Zhang et al., (ACS CHEMICAL BIOLOGY 2013, vol. 8, no. 10, pp 2117-2121) discloses a bovine antibody BLV1H12 comprising an ultralong heavy chain complementarity determining region 3 (CDRH3) fused with a disulfide cross-linked "knob" domain, which is used to incorporate a human erythropoietin (hEPO) into the hypervariable loop of the antibody by substituting hEPO for the "knob" domain, thereby affording an antibody-hEPO fusion protein.

Tao Liu et al. (PNAS 2015, vol. 112, no. 5, pp 1356-1361) describes grafting a hormone into different CDRs of the humanized antibody Herceptin to produce a CDR fusion protein.

Lei Yu et al. (FRONTIERS IN IMMUNOLOGY 2014, vol. 5, Article 250, 1-8) describes the features of a human antibody naïve repertoire comprising long HCDR3s at low frequency.

Muyldermans et al. (CURRENT OPINION IN IMMUNOLOGY 2016, vol. 40, pp 7-13) describes atypical paratopes of camelids and bovines providing the ability to interact with different epitopes, particularly recessed or concave surfaces.

Easterhoff et al. (PLOS PATHOGENS 2017, vol. 13, no. 2, page e1006182) describes vaccine boosted antibodies with long HCDR3 regions.

There is a need for efficient and cost-effective methods to produce long HCDR3 antibodies for diagnostic and therapeutic use. More particularly, there is a need for small, rapidly breeding, animals capable of producing antigen-specific long HCDR3 antibodies.

SUMMARY OF THE INVENTION

This summary is provided to introduce a selection of inventive aspects in a simplified form that are further described below in the detailed description. This summary is not intended to identify key or essential features of the claimed subject matter, nor is it intended to be used to limit the scope of the claimed subject matter. Other features, details, utilities, and advantages of the claimed subject matter will be apparent from the following written detailed description, including those aspects illustrated in the accompanying drawings and defined in the appended claims.

It is the object of the present invention to provide improved means and methods to produce an improved antibody repertoire of functional antibodies.

It is further the objective of the present invention to provide antibody constructs with improved HCHR3 variability, which can be produced in a transgenic animal or in an in vitro cell culture.

The object is solved by the subject of the present claims and as further described herein.

According to the invention there is provided a long DH (LDH)expression cassette comprising a recombinant DH construct comprising at least two DH gene segments encoding at least 10 amino acids of the HCDR3 amino acid sequence, wherein at least one of the DH gene segments is a heterologous DH gene segment. Specifically, such a long DH expression cassette includes at least one heterologous, and in particular non-natively occurring DH gene segment.

In accordance with the foregoing object, transgenic non-human animals are provided which are capable of producing long HCDR3 antibodies and respective antibody repertoires.

Specifically, said heterologous DH gene segment is fused and/or operatively linked to another DH gene segment, thereby obtaining an artificial fusion construct comprising DH gene segments which are not natively associated.

According to a specific embodiment at least two naturally-occurring DH gene segments are fused, thereby obtaining a novel artificial construct is employed as heterologous DH gene segments in the LDH expression cassette.

According to a specific aspect, the heterologous DH gene segment is any of:
 a) a DH gene segment of a different species origin; or
 b) an artificial DH segment comprising
  i) the fusion of at least two naturally-occurring DH gene segments and/or
  ii) a 23 (+/−1) bps recombination signal sequence (RSS); and/or
  iii) the deletion of one or more stop codons; and/or
  iv) the fusion of a DH segment to at least one intergenic region which is artificial or of different species origin.

Introducing a heterologous DH gene segment into the expression cassette provides for modified DH gene segments, which allow the production of antibodies comprising a long HCDR3 sequence, herein referred to as LHCDR3 antibody or LHCDR3 Ab.

By introducing the heterologous DH gene segment, the length of the germline DH gene segments can be increased for generation of LHCDR3 Abs. A long DH (LDH or LDH) gene cassette can be provided that contains one or more e.g., several manipulated (modified) DH gene segments. This cassette can be inserted into the endogenous IgH locus in place of or in addition to the endogenous DH locus.

Specifically, the recombinant DH construct comprises at least two germline DH gene segments.

Specifically, at least two DH gene segments are directly fused DH gene segments, or separate gene segments, connected by an intergenic region. According to a preferred embodiment, at least two human DH gene segments are directly fused, and in particular flanked by an RSS on both ends.

The presence of more than one DH gene segments in a DH expression cassette can be determined by suitable sequencing techniques.

The LDH cassette is typically designed in silico and then created by DNA synthesis or cloning using techniques well known in the art. Once introduced into an animal's (e.g., mouse) genome, the presence, intactness and proper integration of the LDH cassette (e.g., about 9 kb) can be confirmed by targeted locus amplification (TLA), a strategy to selectively amplify large (up to 100 kb) genomic regions on the basis of the crosslinking of physically proximal sequences (de Vree, et al., *Nature Biotechnology* 32:1019-1025 (2014) and next generation sequencing. For example, the entire endogenous DH locus is 7.6 kB in C57BL/6 mice (NCBI Mus musculus strain C57BL/6J chromosome 12, GRCm38.p4 C57BL/6J Sequence ID: NC_000078.6. The DH locus spans positions 113,450,851-113,526,809.) The DH gene segments in the form and sequence described herein do not exist in nature and therefore are easily recognizable and distinguishable from native DH gene segments in a sequenced DH locus.

According to a specific aspect, the recombinant DH construct comprises any of 2-60 different DH gene segments, preferably at least any one of at least 2, 3, 4, 5, 10, 15, or 20 DH gene segments, preferably 5-60 DH gene segments. Specifically, each of the DH gene segments is 20-200 nt long, particularly 31-183 nt, or 31-161 nt long. Specifically, all DH gene segments are comprised in the expression cassette in series, optionally separated by one or more intergenic regions.

Specifically, the HCDR3 amino acid sequence encoded by the DH segments has a length of at least any one of 10, 15, 20, 25, or 30, e.g., up to 70 amino acids, particularly at least 20 amino acids, up to 70, or up to 61 amino acids, or ranging from 20 to 61, or ranging from 20 to 49. Specifically, the HCDR3 amino acid sequence has a length of at least 20, or at least 24, or at least 28 in total, wherein the CDR sequence is designated according to the IMGT system (Lefranc et al., 1999, Nucleic Acids Res. 27: 209-212).

Specifically, said expression cassette is comprised in an arrangement of gene segments which is a V-D(D)x-J arrangement, wherein D is a DH gene segment, and at least one D is a heterologous DH gene segment;
x is one or more, preferably 1-59;
V is a VH gene segment; and
J is a JH gene segment.

According to specific embodiments, any of the following DH gene segments are used as a heterologous DH gene segment:

Bovine DH3.1 mutated to remove stop codons in reading frame (RF) 1-3;
Bovine IGHDS2 in which a sequence encoding a TTVHQ (SEQ ID NO:5) amino acid sequence motif has been appended to the 5' end of the DH;
Fused native human DH gene segments designed in silico and optionally mutated to remove stop codons in RF 1-3;

Synthetic DH (SynDH) gene segments made by bioinformatic identification of long HCDR3 regions expressed by human B cells and converted to SynDH by flanking the N1-DH-N2 sequence of the long HCDR3 with recombination signal sequences.

Specifically, the LDH expression cassette is a cassette of DH gene segments, which may be inserted into a host's endogenous DH and JH genes or loci by standard techniques such as homologous recombination or Recombinase-Mediated Cassette Exchange (RMCE) in embryonic stem cells, in particular of non-human mammals, thereby obtaining the V-D(D)x-J arrangement in the host organism. Such DH gene segment cassette may contain wild-type DH gene segments and/or intergenic regions from the host organism in addition to the heterologous DH genes. The V-D-J locus or the arrangement consisting of V, D and J gene segments, may itself be a transgene expression cassette such as described, for example, in US2013/0219535.

Specifically, said LDH cassette is comprised in a vector that is introduced into a host organism such that said DH genes express a long HCDR3 antibody (LHCDR3 Ab), or participate in VDJ rearrangement in vivo or in vitro, such as further described herein, to produce a long HCDR3 antibody.

Exemplary DH gene sequences are listed in Tables 1-4. Such exemplary DH gene sequences may be used in the construction of one or more heterologous DH sequences or of the recombinant DH construct. For example, sequences listed in Tables 1-4 may be modified to provide a heterologous DH for combination with one or more further DH gene segments.

Table 1 shows mutated bovine long DH gene segments, IGHDS2 (SEQ ID NO:6) and DH3.1 (SEQ ID NO:7).

Table 2 shows a series of human DH gene sequences that have been in silico fused so as to encode long HCDR3 regions. These have also been mutated to remove any stop codons in RF 1, 2, and 3 of the respective native DH gene segments to increase potential antibody diversity. (SEQ ID NO:8-16).

Table 3 shows a series of human DH gene sequences used to encode long HCDR3 regions in normal human B cells. These have been mutated to remove any stop codons in RF 1, 2, and 3 of the respective native DH gene segments to increase potential antibody diversity (SEQ ID NO:17-20).

Table 4 shows long HCDR3 sequences extracted from the IMGT and NCBI databases of expressed Igh cDNAs. These sequences include the N1-DH-N2 portion of the HCDR3 but not the sequences contributed by the 3' part of the VH or the 5' part of the JH and are referred to as Synthetic DH (SynDH) herein. (SEQ ID NO:21-40).

Specifically, the heterologous DH gene segment is a DH gene segment of the same species compared to any one or more of the other DH gene segments comprised in the LDH expression cassette, preferably wherein all DH gene segments are of the same species origin, preferably of human origin.

According to a specific embodiment, a chimeric LDH gene cassette is provided which comprises coding and non-coding sequences of different species origin, or wherein at least one of the coding and non-coding sequences is artificial (non-naturally occurring).

Specifically, the LDH gene cassette comprises a chimeric DH construct, comprising DH gene segments of different species origin.

Specifically, the recombinant DH construct is a chimeric DH construct comprising at least one human DH gene segment and at least one heterologous DH gene segment, which is of different species origin, preferably of bovine origin.

Specifically, at least one of the DH gene segments is of bovine or mouse origin, and at least another one is of human origin to form a chimeric DH expression cassette or vector.

According to a specific aspect, the chimeric LDH gene cassette comprises at least one DH gene segment which is synthetic and/or of non-human mammal origin, and further comprises and at least another DH gene segment which is of human origin.

According to a specific example, any one or more of the DH gene segments is a bovine long DH gene segment, such as bovine long IGHDS2 (147 nt), and/or DH 3.1 (121 nt) gene segment. Specifically, the IGHDS2 can be modified to encode TTVHQ (SEQ ID NO:5) amino acids at the 5' end. In bovine ultralong HCDR3s, this sequence is encoded by the 3' end of the VHBUL gene segment and provides structural integrity to the stalk that supports the HCDR3 knob. By incorporating the sequence encoding the TTVHQ (SEQ ID NO:5) motif into the DH instead of the VH, the amount of genetic manipulations required can be minimized since the VH gene segments will not require modifications, and moreover this modification has the potential to increase the number of VH genes that can be used in ultralong HCDR3 Abs.

```
                                        SEQ ID NO: 5
TTVHQ

SEQ ID NO: 4:
actactgtgcaccag
i.e. the nucleotide sequence encoding SEQ ID NO: 5.
```

According to a specific aspect, an artificial DH segment is used, which a fusion to at least one intergenic region which is artificial or of different species origin. At least one of the DH gene segments may be directly fused e.g., at its 5' and/or the 3' end, to such heterologous intergenic region to obtain a heterologous DH gene segment. Specifically, the recombinant DH construct comprises at least one human DH segment and at least one intergenic region which is of different species origin, preferably of mouse origin. Specifically, at least one of the human DH segments is flanked by at least one mouse intergenic region. Flanked regions are meant to include those which are linked and adjacent to the 5'- and 3' end of the DH gene segment, respectively.

Specifically, one or more of the DH gene segments in a chimeric LDH gene cassette, in particular those of non-murine origin, are flanked by mouse or artificial intergenic regions. Specifically, endogenous human DH gene segments in the cells being targeted are flanked by mouse intergenic regions to form a chimeric DH locus, such as described in US2013/0219535. Specific artificial intergenic regions can be produced by mutating any naturally-occurring intergenic region, or generated synthetically by shuffling naturally-occurring sequences.

Specifically, any one or more of the gene segments contained in the LDH cassette are germline gene segments, which are modified or not.

Specifically, any one or more of the gene segments contained in the LDH cassette are artificial gene segments. Particular examples of artificial gene segments are those comprising nontemplated nucleotide insertions and deletions at gene segment junctions, and/or one or more point mutations, such as an insertion of a CDR sequence, in a germ line gene segment for CDR hypermutation.

By incorporating the heterologous DH gene segment and one or more further DH gene segments described herein, junctional diversity is obtained by DNA sequence variations (also referred to as arrangement or rearrangement) introduced by the joining of gene segments, e.g., during the process of V(D(D)x)J recombination, or by any other suitable in vitro or in vivo techniques. The junctional diversity particularly includes the process of V(D(D)x)J recombination, during which the different variable gene segments (those segments involved in antigen recognition) of immunoglobulins are rearranged. The antibody diversity is even more expanded by the choice of further DH segments and/or further sequence-level modifications and respective mutagenesis.

Specifically, any of the DH gene segments can be mutated to remove stop codons. Specifically, the heterologous DH gene segment is an artificial DH segment that is mutated to remove stop codons, in particular in one or more of reading frames (RF) 1, 2 and 3.

According to a specific aspect, a recombinant DH construct is provided which comprises a combination and/or fusion of a series of DH gene segments (e.g., 5-60 gene segments that are each 31-161 nt in length. Each DH gene segment can be flanked by RSS and the construct may also include intergenic regions, making the total length of the LDH cassette e.g., within the range of 8-10 kB, in particular about 9 kB. The cassette can be created by any of in vitro, or in vivo recombination methods, or by in silico joining of DH gene segments, in particular using native human DH gene segments.

In addition to being artificially fused or otherwise recombined, any one or more, in particular all stop codons in RF 1, 2 and 3 can be eliminated to increase the potential diversity of DH gene segments.

According to a specific embodiment, all DH gene segments can be used in all six RF. RF1-3 can be used when VDJ rearrangement occurs by deletion, and RF4-6 can be used when VDJ rearrangement occurs by inversion. Yet, although the DH gene segments can potentially be used in multiple reading frames, typically one RF is preferred. According to a typical example, in addition to increasing DH length by incorporation of fused D's in the germ line, DH diversity is increased by eliminating all stop codons in RF 1-3, which contribute to >90% of Ig HC rearrangements. Bioinformatic analyses of sequence databases may further be used to identify antibody heavy chains that have longer than average HCDR3 regions. These HCDR3s can be artificially flanked with appropriate RSS and incorporated into the DH locus so that they can be utilized in forming the primary HC repertoire and lengthened even further during VDJ rearrangement by the normal physiological process of incorporating portions of the V and J regions, N sequence addition described herein.

Any of the naturally-occurring long human germline DH segments may be used to produce the LDH expression cassette described herein. According to specific examples, the LDH gene cassette described herein comprises different types of DH segments. In one example, two DH gene segments that are adjacent to each other in the native human DH locus are fused. If the neighboring DH gene segments are too short to achieve a minimal desired length e.g., of 30 nt or more, such as 31 nt, it is preferred to fuse another neighboring DH gene segment. Alternatively, randomly selected DH gene segments can be fused.

According to a specific aspect, the heterologous DH gene segment is a bovine IGHDS2 gene segment, or any other bovine DH-2 gene segment which is modified to encode an amino acid sequence identified as SEQ ID NO:5 (TTVHQ) at its 5' end.

For example, any of a human germline DH gene segment D2-2 (31 nt in length), D2-15 (31 nt) and D3-16 (36 nt) that are longer than the average DH (27 nt) and have been described by Briney et al. (PLoS ONE, e36750, 2012) as expressed by normal human be cells are mutated to remove RF1-3 stop codons to further diversify long HCDR3s.

Figure 3:

According to a specific example, a recombinant DH construct is synthesized or otherwise provided which corresponds to the HCDR3 region of LHCDR3 Abs in human sequences except for that portion of the HCDR3 contributed by the V and J gene segments (FIG. 3). Such a DH, termed here synthetic DH (SynDH) consists of N sequences flanking the original DH that were introduced during VDJ rearrangement to create the LHCDR3 Ab, as well as the DH itself. This DH does not typically contain the entire germline DH sequence since there is usually some nibbling of the ends of the DH gene segment during VDJ rearrangement. The SynDH gene segments provide a template to create a novel DH gene repertoire for producing a diverse repertoire of LDH expression cassettes as described herein.

Specifically, any of the DH gene segments can be mutated to introduce a RSS, which is compatible with joining to another DH gene segment. In particular, an artificial DH gene segment is used which comprises a RSS that is modified and extended to include a 23 (+/−1) bp RSS spacer, some examples of which are shown in SEQ ID NOs: 1-3, each of which consists, left to right of a heptamer, spacer (underlined, the RSS spacer can be exchanged for any suitable alternative spacer of the same length) and a nonamer sequence.

```
23 bp RSS
                                         SEQ ID NO: 1
CACAGTG AGGGGAAGTCAGCGAGAGCCCAG ACAAAAACC 23 bp RSS
                                         SEQ ID NO: 2
CACAGTG AGGGGAGGTGAGTGTGAGCCCAG ACAAAAACC 23 bp RSS
                                         SEQ ID NO: 3
CACAGTG ACACAGCCCAGGGCACCTCCTGT ACAAAAACC
```

RSS typically used comprise a conserved heptamer and a conserved nonamer motif, separated by a spacer of defined length e.g., either 12+/−1 bp or 23+/−1 bp long. Naturally-occurring DH gene segments comprise a RSS including a 12 bp long spacer at both of its ends, allowing recombination with a VH and a JH gene segment (each comprising a 23 bp RSS spacer) and inhibiting a DH-DH (D>D) arrangement, according to the 12/23 bp rule.

Yet, the artificial DH gene segment preferably used herein comprises and is particularly flanked by a RSS including a 23 bp long spacer, at one or both of its 5' and 3' ends, allowing further recombination with at least another DH gene segment that comprises the RSS including the 12 bp spacer. For example, a series of artificial DH gene segments can be used which are flanked by compatible RSS, i.e., 12 and 23 bp, allowing the arrangement of a D>D 12/23 bp combination in series.

According to a specific approach described herein random DH-DH fusions are produced to increase HCDR3 length, e.g., by altering the RSS spacer lengths of the rearranging gene segments so that D>D>J rearrangements occur much more frequently than normal. DH-DH fusions described herein, e.g., obtained by incorporating synthetic D-D fusions into the germline Igh locus of a host, or by manipulating the RSS lengths can lead to functional VD(D)xJ arrangements. Such arrangement, although very rare in normal B cells, can occur and the resultant heavy chain can be expressed by B cells Antibodies described herein are specifically characterized by the long HCDR3 (LHCDR3) amino acid sequence; such antibodies are herein referred to as long HCDR3 antibodies (LHCDR3 Ab). According to a specific embodiment, the LHCDR3 is encoded by a VH-DH-JH exon, wherein the long germline DH gene segments (LDH) are incorporated into this exon during normal VDJ rearrangements in developing B lymphocytes, thereby obtaining the V-(D(D)x)-J arrangement as described herein.

The LHCDR3 Ab obtainable by expression and production methods described herein are particularly characterized by unique HCDR3 sequences which correspond to the DH portion of the expression cassette. In particular, antibodies are provided which comprise a HCDR3 sequence incorporating any of the sequences listed in any of the Tables 1-4 and optionally combined with a further HCDR3 sequence thereby obtaining a long hHCDR3 sequence. Specifically, the LHCDR3 Ab comprise a chimeric HCDR3 sequence.

The invention further provides for an immunoglobulin library (also referred to as repertoire) comprising a diversity of at least 10E3 library members, which differ in the HCDR3 amino acid sequence, each with a DH length of at least 10 amino acids, e.g., at least any one of 10, 15, 20, 25, or 30, e.g., up to 70 amino acids, particularly ranging from 10-61 amino acids, or ranging from 10-49.

The library provided herein specifically comprises a repertoire of LHCDR3 Abs, but may still comprise further antibodies which are characterized by a HCDR3 with a different length.

According to a specific aspect, the invention provides for a repertoire of antibodies comprising the LHCDR3 Ab described herein, which repertoire comprises a diversity of antibodies which differ in at least one mutation in the CDR region, each specifically recognizing the same target antigen. Such repertoire is understood as an antibody library of the same antibody type or structure, wherein antibodies differ in their antigen-binding sites, e.g., to produce antibody variants of a parent antibody recognizing the same epitope, such as affinity matured or otherwise optimized antibody variants; or antibodies that specifically recognize a target antigen, but different epitopes of such target antigen.

Such repertoire can be suitably screened and individual library members can be selected according to desired structural or functional properties, to produce an antibody product.

According to a specific aspect, the invention provides for a repertoire of antibodies comprising the LHCDR3 Ab described herein, which repertoire comprises a diversity of antibodies, recognizing different target antigens. Such a repertoire is obtained by immunization with complex, multicomponent antigens such as viruses or bacteria which have many different target antigens, each of which has multiple epitopes.

According to a specific embodiment, the repertoire is understood as a naïve library of antibodies, also termed the pre-immune repertoire, which is expressed by mature but antigen-inexperienced B cells that have recently exited from the bone marrow, their site of generation.

The repertoire of antibodies described herein is specifically characterized by a diversity encompassing at least $10^3$ antibodies, preferably any of at least $10^4$, $10^5$, $10^6$ or $10^7$, each characterized by a different antigen-binding site.

According to a specific aspect, the repertoire described herein is provided, wherein
 a) genes encoding said antibodies are derived from B cells of non-immune or immunized mice, or
 b) the antibodies are secreted by mammalian plasmacytes, preferably of rodent origin, in particular of mouse origin.

Specifically, the repertoire is obtainable by cloning the genes encoding it from B cells or by secreting the antibodies by a variety of mammalian plasmacytes. Specifically, the antibodies secreted by mammalian plasmacytes are characterized by a glycosylation pattern that is characteristic of the species of origin of the mammalian plasmacytes. Most physiological antibody isotypes are secreted as dimers of H2L2 but IgA can also be secreted as a dimer $(H2L2)_2$ or trimer $(H2L2)_3$ and IgM can be secreted as a pentamer $(H2L2)_5$ or hexamer $(H2L2)_6$.

According to a specific aspect, a method of producing the antibodies is described herein, and specifically a method of producing the repertoire of antibodies described herein by engineering mammalian plasmacytes expressing and secreting such antibodies employing the LDH expression cassette described herein.

Specifically, the mammalian plasmacytes are of non-human animal origin, e.g., of mammalian, vertebrate origin, in particular, a rodent such as mouse, or rat; or rabbit, or avian origin, such as chicken. Specifically, the mammalian plasmacytes originate from a rodent, preferably mouse.

According to a specific embodiment, the antibody is produced in a host cell (in vitro) or in a non-human animal host (in vivo).

Specifically, the genes encoding one or more HCs and optionally one or more LC of the LHCDR3 Ab are expressed in such host or host cell, respectively. According to a specific aspect, a host cell is engineered by incorporating the LDH expression construct into an immunoglobulin heavy chain locus.

The invention further provides for an immunoglobulin heavy chain locus comprising the expression cassette described herein, which is functional to express said HCDR3 amino acid sequence, e.g., in vitro in a cell culture, or in vivo in a transgenic non-human host animal.

The invention further provides for a transgenic non-human animal comprising the immunoglobulin heavy chain locus described herein, or the expression cassette described herein, preferably a mouse, rat, rabbit or chicken locus. The transgenic non-human animal is preferably of any of mouse, rat, rabbit or chicken species and includes such locus of the same species.

Specifically, the transgenic non-human animal comprises loss-of-function mutations within, or deletion of, the endogenous DH locus. Specifically, the transgenic animal comprises the functional exogenous DH locus and the respective LDH expression cassette to express a LHCDR3 Ab after VDJ rearrangement.

The invention further provides for a method for generating a transgenic non-human animal comprising:
 a) providing a non-human animal cell, preferably an embryonic stem cell;
 b) providing one or more vectors, each comprising at least one cassette containing gene segments that upon VDJ or VJ rearrangement encode immunoglobulin sequences;
 c) introducing said one or more vectors into said non-human animal cell;
 d) incorporating said gene segments into the genome of said non-human animal cell, and selecting a transgenic cell wherein said gene segments have been integrated into the cellular genome of said non-human animal cell; and
 e) utilizing said transgenic cell to create a transgenic non-human animal comprising said transgenic cell;
wherein at least one of said vectors comprises the expression cassette described herein. Specifically, the LDH expression cassette as described herein is used, which comprises DH gene segments encoding the core HCDR3 amino acid sequence of a LHCDR3 Ab, i.e. the HCDR3 sequence that encodes the 5'N-DH-3'N part of the HCDR3 (see FIG. 3).

According to a specific embodiment, a method for generating a transgenic non-human animal is described herein, comprising:
 a) providing a non-human animal cell, comprising a functional immunoglobulin heavy chain locus;
 b) providing one or more vectors comprising the LDH expression cassette comprising the DH gene segments modified for production of the LHCDR3 Ab as described herein;
 c) introducing said one or more vectors into said non-human animal cell;
 d) incorporating said LDH expression cassette into the genome of said non-human animal cell, and selecting a transgenic cell wherein said DH gene segments have been integrated into the cellular genome of said non-human animal cell at a target site which replaces the endogenous immunoglobulin DH locus; and
 e) utilizing said transgenic cell to create a transgenic non-human animal comprising said transgenic cell.

The transgenic non-human animal can be used to produce a LHCDR3 Ab, or a LHCDR3 Ab repertoire.

According to a specific aspect, the non-human transgenic animal described herein is provided for use in a method of producing an immunoglobulin comprising said HCDR3 amino acid sequence, in particular a LHCDR3 Ab.

Specifically, the non-human transgenic animal described herein is used for producing a library comprising a diversity of immunoglobulins which differ in at least the HCDR3 amino acid sequence in particular a LHCDR3 Ab repertoire.

According to a specific aspect, a transgenic non-human animal is provided which comprises
 a) a functional immunoglobulin heavy chain locus comprising
  i) a variable heavy chain region comprising one or more of each of the VH, DH and JH gene segments,
  ii) a constant heavy chain region comprising constant exons encoding the CH1, CH2, and CH3 domains of all the HC isotypes, and
 b) a functional immunoglobulin κ light chain locus comprising one or more of each of the Vκ and Jκ gene segments and a constant light chain region comprising the exon encoding a Cκ domain,
 c) a functional immunoglobulin λ light chain locus comprising one or more of each of the Vλ and Jλ gene segments and constant light chain regions comprising exons encoding Cλ domains,
which regions are engineered to express a LHCDR3 Ab described herein.

In particular, an LDH expression cassette is used in said immunoglobulin heavy chain locus.

Specifically, the immunoglobulin heavy chain locus is heterologous or a recombinant locus, which is originating from an animal's endogenous locus, yet comprising at least one exogenous element, e.g., one or more exogenous heavy chain regions, not natively associated with one or more further elements of the locus.

Specifically, an expression vector is used, which upon transfection of a host cell recombines with the host cell genome and, following productive VDJ rearrangement, the encoded antibody is expressed and secreted by the host cell.

Specifically, a vector described herein comprises one or more exogenous or heterologous regulatory elements, such as a promoter operably linked to the antibody coding sequence, which regulatory elements are not natively associated with said antibody coding sequence.

According to a specific aspect, the invention provides for a recombinant host cell comprising the heterologous immunoglobulin heavy chain locus, or an expression cassette or vector described herein.

According to a specific aspect, the invention provides for a host cell transfected with the immunoglobulin heavy chain locus described herein, or the vector described herein.

Specifically, the transgenic non-human animal described herein is a mammalian, such as a vertebrate, in particular, a rodent such as mouse, or rat; or rabbit, or a bird, such as chicken.

Preferably, the transgenic non-human animal is a rodent, preferably a mouse.

Specifically, the transgenic non-human animal is avian, and the animal is produced using primordial germ cells. Thus, the methods described herein may further comprise: isolating a primordial germ cell that comprises the introduced antibody coding regions and using said germ cell to generate a transgenic non-human animal that contains the replaced immunoglobulin locus.

Specifically, the transgenic non-human animal carries modified immunoglobulin alleles or other transgenes in their genomes:

In a specific embodiment, the transgenic animals of the invention further comprise human immunoglobulin regions. For example, numerous methods have been developed for replacing endogenous mouse immunoglobulin regions with human immunoglobulin sequences to create partially- or fully-human antibodies for drug discovery purposes. Examples of such mice include those described in, for example, U.S. Pat Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669.

In the particularly favored aspects, the transgenic animals of the invention comprise chimeric immunoglobulin segments as described in US 2013/0219535 by Wabl and Killeen. Such transgenic animals have a genome comprising an introduced partially human immunoglobulin region, where the introduced region comprising human variable region coding sequences and non-coding regulatory sequences based on the endogenous genome of the non-human vertebrate. Preferably, the transgenic cells and animals described herein have genomes in which part or all of the endogenous immunoglobulin region is removed and/or engineered to incorporate heterologous genes or gene segments.

In another favored aspect, the genomic contents of animals are modified so that their B cells are capable of expressing more than one functional VH domain per cell, i.e., the cells produce bispecific antibodies, as described in WO2017035252A1.

In another favored aspect, the genomic contents of animals are modified so that their B cells are capable of expressing antibodies composed of heavy chains but no light chains, i.e., the cells produce heavy chain-only antibodies.

Specifically, a marker is used to indicate the successful integration of said gene segments or exons into the cellular genome. Specifically, the marker is a selectable marker, which is capable of expression in a host that allows for ease of selection of those hosts containing an introduced nucleic acid or vector.

Examples of selectable markers include, e.g., proteins that confer resistance to antimicrobial agents (e.g., puromycin, hygromycin, bleomycin, or chloramphenicol), proteins that confer a metabolic advantage, such as a nutritional advantage on the host cell, as well as proteins that confer a functional or phenotypic advantage (e.g., cell division) on a cell.

Specifically, the vector is introduced such that the coding nucleic acid sequence is inserted into the cell, by means capable of incorporation of a nucleic acid sequence into a eukaryotic cell wherein the nucleic acid sequence may be present in the cell transiently or may be incorporated into or stably integrated within the genome (in particular within a chromosome) of the cell.

Specifically, said exons are integrated into the cellular genome of said non-human animal cell at a target site, by any methods of targeted recombination, e.g., by homologous recombination or by site-specific recombination techniques. Specifically, the CRISPR/Cas9 genome editing system may be used for targeted recombination (He, et al., Nuc. Acids Res., 44:e85, 2016).

Specifically, said non-human animal cell is an embryonic stem (ES) cell of a said non-human animal. In one aspect, the host cell utilized for replacement of the endogenous immunoglobulin genes is an ES cell, which is then utilized to create a transgenic mammal. Thus, specific methods described herein may further comprise: isolating an ES cell that comprises the introduced antibody coding regions and using said ES cell to generate a transgenic animal that contains the engineered or replaced immunoglobulin locus.

According to a specific embodiment, a method for generating a transgenic non-human animal is provided, comprising:

a) providing a non-human animal cell comprising a functional immunoglobulin heavy chain locus and integrating into its genome via a homology targeting vector a first set of sequence-specific recombination sites into a region upstream of the heavy chain DH locus;

b) integrating into the genome of said non-human animal cell a second set of sequence-specific recombination sites into a region downstream of the heavy chain DH locus;

c) deletion of the region between the first and second set of sequence-specific recombination sites, including the heavy chain DH locus, and creating a recombinase-mediated cassette exchange (RMCE) target site at that location by introducing a recombinase corresponding to the sequence-specific recombination sites introduced into the genome of said non-human animal cell;

d) providing one or more vectors comprising the LDH cassette comprising the DH gene segments modified for production of the LHCDR3 Ab described herein, which gene segments are flanked by further recognition sites for a site-specific recombinase, and one or more markers to select for targeted integration of the vector into a cellular genome, wherein the further recognition sites are capable of recombining with said RMCE target site;

e) introducing said one or more vectors and a site-specific recombinase recognizing said RCME target site and further recognition sites, into said non-human animal cell;

f) incorporating said LDH cassette into the genome of said non-human animal cell, and selecting a transgenic cell wherein said exons have been integrated into the cellular genome of said non-human animal cell at said RMCE target site; and g) utilizing said transgenic cell to create a transgenic non-human animal comprising said transgenic cell.

Specifically, any of said recognition sites for a site-specific recombinase is a recombinase recognition site (e.g., Cre/lox, Flp-FRT, etc.), where the recombinase is capable of excising a DNA sequence between two of its recognition sites.

Specifically, a homology targeting vector or "targeting vector" may be used, which is a vector comprising a nucleic acid encoding a targeting sequence, a site-specific recombination site, and optionally a selectable marker gene, which is used to modify an endogenous immunoglobulin region using homology-mediated recombination in a host cell. For example, a homology targeting vector can be used in the present invention to introduce a site-specific recombination site into particular region of a host cell genome.

According to a specific aspect, a method for producing a LHCDR3 Ab is further provided herein, comprising:

a) expressing a heterologous immunoglobulin heavy chain DH locus in a non-human animal comprising functional immunoglobulin heavy and light chain loci; and b) producing said LHCDR3 Ab, wherein a LDH cassette described herein is used in VDJ rearrangement to express the HCDR3 sequence of said LHCDR3 Ab.

Specifically, a functional immunoglobulin heavy chain locus comprises all elements to express a functional heavy chain of an antibody in a mammalian cell, which locus comprises at least VH domains, constant domains (in particular CH1, CH2, and CH3) and a hinge region.

Specifically, the non-human animal comprises the immunoglobulin heavy chain DH locus described herein.

According to a specific aspect, a method for producing an antibody is provided herein, comprising expressing in a non-human animal:

a) an immunoglobulin heavy chain locus comprising
i) a variable heavy chain region comprising one or more of each of the VH, DH and JH gene segments, wherein the DH gene segments are comprised in a LDH expression cassette described herein;
ii) a constant heavy chain locus comprising constant exons encoding all Ig isotypes;
and b) optionally a variable light chain locus comprising
i) a variable light chain region comprising one or more of each of the VL and JL gene segments; and
ii) a constant light chain region comprising constant exons encoding a LC domain;
and c) isolating the LHCDR3 Ab described herein.

Specifically, the method further comprises the method step:

d) producing an antibody or antibody fragments comprising at least the VH domain of said LHCDR3 Ab.

Such further method step d) is typically performed in vitro, e.g., by identifying the sequence of the produced LHCDR3 Ab or the nucleic acids encoding the same, and producing the antibody or antibody fragments in a cell culture. Such antibody can be a LHCDR3 Ab, or any other antibody comprising the VH domain of said LHCDR3 Ab, or at least the antigen-binding part thereof, which is incorporated in a different antibody format, e.g., a full-length antibody or an antibody fragment comprising said VH domain. Said VH domain may be used to engineer antibodies comprising said VH in the original form, or further engineered to incorporate a limited number of point mutations e.g., to produce an affinity matured VH domain.

Specifically, the non-human animal is treated to incorporate a heterologous locus by suitable gene targeting techniques, e.g., directed homologous recombination, employing site-specific recombinase techniques, or CRISPR/Cas9 techniques.

Specifically, the non-human animal is the transgenic non-human animal of the invention and further described herein.

According to a specific embodiment, the method further comprises the step of immunizing the non-human animal with an antigen such that an immune response is elicited against that antigen resulting in the generation of affinity-matured specific monoclonal or polyclonal antibodies.

An antigen can be administered to the non-human animal in any convenient manner, with or without an adjuvant, and can be administered in accordance with a predetermined schedule.

After immunization, serum or milk from immunized animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethylene glycol.

For making a monoclonal antibody, antibody-producing cells, e.g., spleen and/or lymph node cells, may be isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art.

Specifically, the method further comprises the steps of preparing hybridomas and the producing and screening antibody producing cells, in particular those which specifically recognize a target antigen.

Specifically, the method further comprises the step of isolating nucleic acid sequences from the immunized non-human animal for the production of specific antibodies, or fragments thereof, in particular antigen-binding fragments, in a cell culture. Such antibodies or antigen-binding fragments thereof are herein understood as hyperimmune antibodies.

According to a specific embodiment, the antibodies described herein are produced in a cell culture employing suitable production host cell lines. Specifically, the production employs bacterial, yeast, plant, insect, or mammalian cell culture, in particular a eukaryotic cell culture. Specifically, the host cells are used upon recombination with the respective nucleic acid molecules encoding the antibodies described herein. In particular, any of the mammalian host cells are advantageously used: BHK, CHO, HeLa, HEK293, MDCK, NIH3T3, NS0, PER.C6, SP2/0 or VERO cells.

According to a specific aspect, the invention provides for the use of the transgenic non-human animal described herein for producing a LHCDR3 Ab, or fragments thereof including at least the VH domain of said LHCDR3 Ab, and optionally for further producing an antibody comprising said VH domain.

According to a specific aspect, the invention provides for the use of the transgenic non-human animal described herein for producing a library, in particular a naïve library of LHCDR3 antibodies, or fragments thereof including at least the VH domain of a selected LHCDR3 Ab, or a library of nucleic acid sequences encoding or expressing said naïve library.

Transgenic cells described herein may be used to produce expression libraries for identifying antibodies of interest, e.g., by cloning the genes encoding the antibodies from B cells, or by selecting plasma cells with defined specificity in engineered mice that express antibodies on the plasma cell membrane. The present invention thus also includes antibody libraries produced using the cell technologies for the identification of antigen-specific antibodies expressed on plasma cells.

Upon producing the LHCDR3 Ab described herein, its VH domain or its antigen-binding site can be characterized by suitable techniques to engineer an antibody of any type, e.g., full-length antibodies or antigen-binding fragments thereof, heavy chain only antibodies, or even single VH domain antibodies and antibody constructs comprising such single VH domain antibodies. For example, the amino acid sequence or the coding nucleotide sequence of the VH domain or its antigen-binding site can be determined and recombined with further sequences of an antibody construct, or other binding molecules incorporating such VH domain or its antigen-binding site.

Some exemplary embodiments provide transgenic animals of the invention, which are further comprising human immunoglobulin regions. For example, numerous methods have been developed for replacing endogenous mouse immunoglobulin regions with human immunoglobulin sequences to create partially- or fully-human antibodies for drug discovery purposes. Examples of such mice include those described in, for example, U.S. Pat Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669.

Some further exemplary embodiments provide transgenic animals of the invention, which are further comprising chimeric immunoglobulin segments as described in US 2013/0219535 by Wabl and Killeen. Such transgenic animals have a genome comprising an introduced partially human immunoglobulin region, where the introduced region comprising human variable region coding sequences and non-coding variable sequences based on the endogenous genome of the non-human vertebrate. Preferably, the transgenic cells and animals of the invention have genomes in which part or all of the endogenous immunoglobulin region is removed.

Some further exemplary embodiments provide transgenic animals of the invention, which are further comprising changes to the immunoglobulin heavy chain gene allow for production of bispecific antibodies as described in WO2017035252A1, or for production of antibodies composed of one or more HCs, but no LC.

Other embodiments provide primary B cells, immortalized B cells, or hybridomas derived from the genetically modified animal.

Other embodiments include a part or whole immunoglobulin protein transcribed from the immunoglobulin heavy chain genes from the engineered portion of the genetically modified animal; and part or whole engineered immunoglobulin proteins derived from the cells of the genetically modified animal.

According to a specific aspect, antibodies and respective libraries may be produced, which are either full-length immunoglobulins, antigen-binding antibody fragments thereof, or any other antibody construct that comprises at least a variable heavy chain (VH) antibody domain, such as Fab, F(ab'), (Fab)$_2$, scFv, Fd, Fv, or a full-length antibody, e.g., of an IgG type (e.g., an IgG1, IgG2, IgG3, or IgG4 subtype), IgA1, IgA2, IgD, IgE, or IgM antibody. A particular embodiment is a heavy chain only antibody, which consists of only one HC, which comprises an antigen-binding VH domain optionally paired with a VL domain.

Specifically, the LHCDR3 Ab comprises an antigen-binding site that comprises the HCDR3 described herein. According a certain aspect, the HCDR3 described herein determines the specificity of antigen-binding. Specifically, the HCDR3 does not include fusion with a biologically active protein, in particular to avoid any interference of the LHCDR3 Ab bindig to the respective target antigen by its antigen-binding site.

Specifically, the antigen-binding part of a LHCDR3 Ab described herein is composed of heavy chains (HC) and light chains (LC), wherein the antigen-binding site of one HC and one LC in combination specifically comprises or consists of the three CDR loops of the VL domain comprised in a LC, i.e., LCDR1, LCDR2, and LCDR3, and three CDR loops of the VH domain comprised in a HC, i.e., HCDR1, HCDR2, and HCDR3. These CDRs are specifically of normal physiological length, which varies somewhat depending on the species, except for HCDR3, which is longer than naturally-occurring or longer than in a wild-type organism, due to incorporation of a long DH from the LDH cassette into the VH-encoding exon.

According to another specific embodiment, the antigen-binding part of a LHCDR3 Ab is comprised in a VH antibody domain only, wherein the antigen-binding site comprises or consists of the three CDR loops of the VH domain, i.e., HCDR1, HCDR2, and long HCDR3.

Yet, according to another specific embodiment, the antigen-binding part of the LHCDR3 Ab is composed of a heavy chain (HC) only, wherein the antigen-binding site comprises or consists of CDR loops, including the long HCDR3, which are comprised in one or more variable domains comprised in the HC. For example, the antigen-binding part is of a heavy-chain antibody, or heavy-chain only antibody.

The antigen-binding site can be further mutated to increase the diversity and/or to change the binding affinity e.g., can be affinity matured by variation of one or more of the CDR loops thereby optimizing or increasing affinity of binding a target antigen. A mutated antigen-binding site can be obtained by one or more point mutations, e.g., 1, 2, 3 or more point mutations in any or each of the CDR sequences e.g., to obtain an affinity matured antigen binding site, through a suitable in vivo process, or by employing in vitro mutagenesis techniques.

Antibodies produced by a transgenic non-human animal, are commonly understood as natural or native antibodies. Such natural antibodies can derive from the naïve repertoire or undergo affinity maturation in vivo resulting in high affinity antibodies that bind a specific target antigen, e.g., with a $K_D$ of less than $10^{-7}$ M, e.g., between $10^{-7}$ and $10^{-10}$ M.

Affinity matured antibodies produced by in vitro mutagenesis methods, such as employing random mutagenesis and/or library techniques, can result in even higher affinities, e.g., with a $K_D$ of less than $10^{-8}$ M, e.g., less than $10^{-11}$ M.

Natural antibodies advantageously are characterized by a native conformation of VH- and VL-CDR sequences. Such native conformation is characterized by a naturally-occurring primary structure of the antigen-binding site, and/or the naturally-occurring primary structure of the full-length VH and VL domains.

The native conformation of a VH or VL domain can be produced in vivo e.g., upon mutating CDR sequences of a parent domain, or by producing variants of a parent VH or VL domain, using artificial antibody display systems and respective libraries containing artificial antibody sequences, which can be selected to produce suitable antibodies.

The LHCDR3 Ab may specifically comprise an Fc region.

The Fc region described herein specifically comprises the constant region of an antibody excluding the first constant region immunoglobulin domain. Thus "Fc region" refers to the last two constant region immunoglobulin domains of IgA, IgD, and IgG, and the flexible hinge N-terminal to these domains, and the last three constant region immunoglobulin domains of IgE and IgM. For IgG, Fc comprises immunoglobulin domains CH2 and CH3 (Cγ2 and Cγ3) and the hinge between CH1 (Cγ1) and CH2 (Cγ2). The Fc region may also comprise a CH2 or CH3 domain in the form of an artificial variant of a respective naturally occurring antibody domain, e.g., with at least 90% sequence identity to said naturally occurring antibody domain.

In particular, the Fc region described herein comprises or consists of a dimer of CH2 and CH3 domains which domains are part of an antibody heavy chain (HC), wherein the CH2 domain of a first HC is paired with the CH2 of a second HC, and the CH3 domain of the first HC is paired with the CH3 of the second HC. Such dimer may be a homodimer, i.e., composed of two CH2-CH3 domain chains of the same amino acid sequence, or a heterodimer, i.e., composed of two CH2-CH3 domain chains, wherein each has a different amino acid sequence, e.g., with different CH3 amino acid sequences for stabilizing the Fc.

The LHCDR3 Ab specifically comprises a hinge region connecting a CH2-CH3 domain chain of the Fc region to a heavy chain part of a Fab arm.

Specifically, the hinge region is originating from an antibody heavy chain hinge region linking the C-terminus of a CH1 domain to the N-terminus of a CH2 domain. Alternatively, any other natural or artificial linker of about the same length can be used. Suitable hinge regions are native (naturally occurring e.g., human or mouse) IgG or IgA heavy chain hinge regions, or functional variants thereof of the same length +/−1 or 2 amino acids, which optionally contain one or more, up to 5 or fewer point mutations. The hinge region typically comprises one or more cysteine residues to produce disulfide bridges in the LHCDR3 Ab, such as to connect two HCs.

Specifically, the amino acid sequences of two HCs comprised in the LHCDR3 Ab (herein also referred to as the first and the second HC) are identical. Alternatively, the amino acid sequences of the two HCs differ e.g., such that the antigen binding sites of the VH domains are different.

For example, the first HC comprises a first VH, and the second HC comprises a second VH. The first and second VHs may comprise the same or different antigen-binding sites, e.g., specifically recognizing two different target antigens. Therefore, the LHCDR3 Ab can be monospecific, bivalent, or bispecific.

When producing LHCDR3 Ab, selected antibody domains and/or hinge regions are of human, artificial, or non-human animal origin. For example, the LHCDR3 Ab is produced in a transgenic mouse, comprising human and mouse sequences.

According to a specific aspect, the LHCDR3 Ab described herein is provided in the soluble form, e.g., water-soluble form at concentrations suitably used in a pharmaceutical preparation. Specifically, a soluble preparation comprising the LHCDR3 Ab is provided in the isolated form, such as isolated from serum or a blood fraction of an animal producing the same, or isolated from a cell culture fraction.

According to a specific aspect, the invention provides for the LHCDR3 Ab described herein, for medical use.

Accordingly, a method of treating a subject is described herein, e.g., the medical treatment of a human being or a non-human mammal, for prophylaxis or therapy of a disease, which comprises administering to said subject an effective amount of said LHCDR3 Ab.

According to a specific aspect, the invention provides for nucleic acid molecules encoding the LHCDR3 Ab described herein. Specifically, one of the nucleic acid molecules encodes the HC chain composed of antibody domains VH-CH1-hinge-CH2-CH3; and another nucleic acid molecule encodes the LC composed of a VL-Cκ domain.

These and other aspects, objects and features of the invention are described in more detail below.

FIGURES

FIG. 1: Depicts the mouse Igh locus (top) [including V (IghV), D (IghD), J (IghJ), and C (IghC) gene segments] and Igk locus (bottom) [including V (IgkV), J (IgkJ), and C (IgkC) gene segments]. Also shown are 1) PAIR elements, which are cis-regulatory sequences critical for Igh looping to ensure utilization of distal VH gene segments in VDJ rearrangements, 2) the Adam6a male fertility-enabling gene, 3) Intergenic Control Region 1 (IGCR1), which contains sites that regulate ordered, lineage-specific rearrangement of the Igh locus, 4) Eμ, the heavy chain intronic enhancer, 5) Sμ, the switch region, 6) the 3' regulatory region (3'RR), a cis-acting element that controls isotype switching, and 6) Eκ, the κ light chain intronic enhancer.

Figure 2:
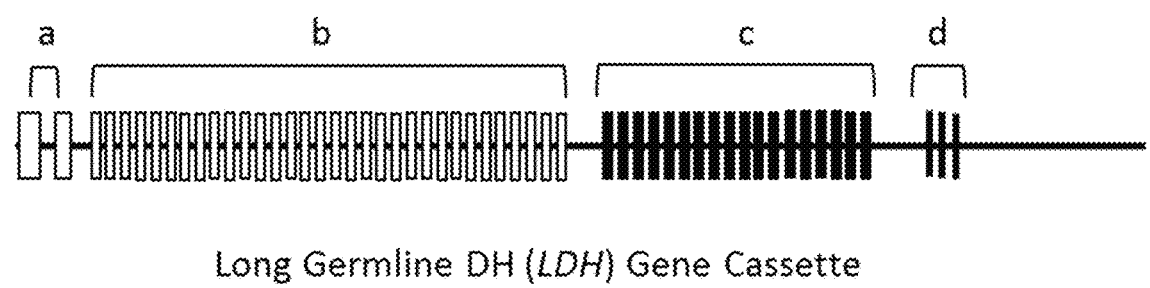

FIG. 2: Depicts an exemplary LDH gene cassette that is used to replace or in addition to the endogenous DH locus. The indicated elements of the cassette, which are described in detail in Example 1, are: a. bovine DH segments, b. fused DH segments, c. synthetic DH segments, d. long DH segments. The order of the different modified DH gene segments in the cassette is shown as a single example, as these gene segments can be inserted into the cassette in any order or frequency desired.

FIG. 3: Depicts the composition of the HCDR3 in a normal antibody H chain (left), with contribution from the 3' end of the VH gene segment, the DH gene segment and the 5' end of the JH gene segment, as well as non-templated (N) sequences added at the 5' (N1) and 3' (N2) sides of the DH during VDJ rearrangement. On the right is the synthetic DH (SynDH) that is one of the components of the LDH cassette, consisting of core N1-DH-N2 from the HCDR3 now flanked by recombination signal sequences (RSS) to allow for participation in VDJ rearrangement.

Figure 4:
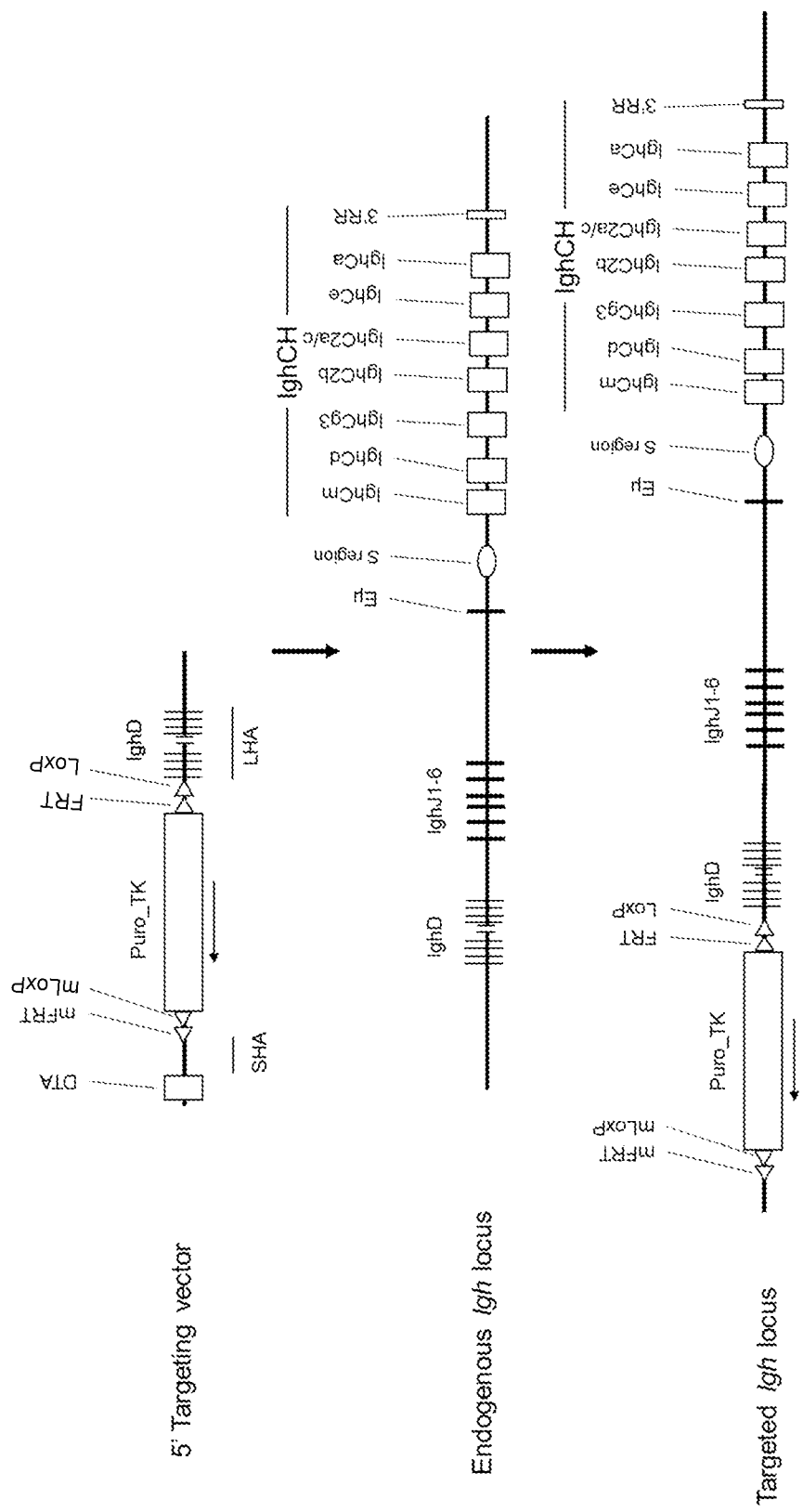
Figure 5:
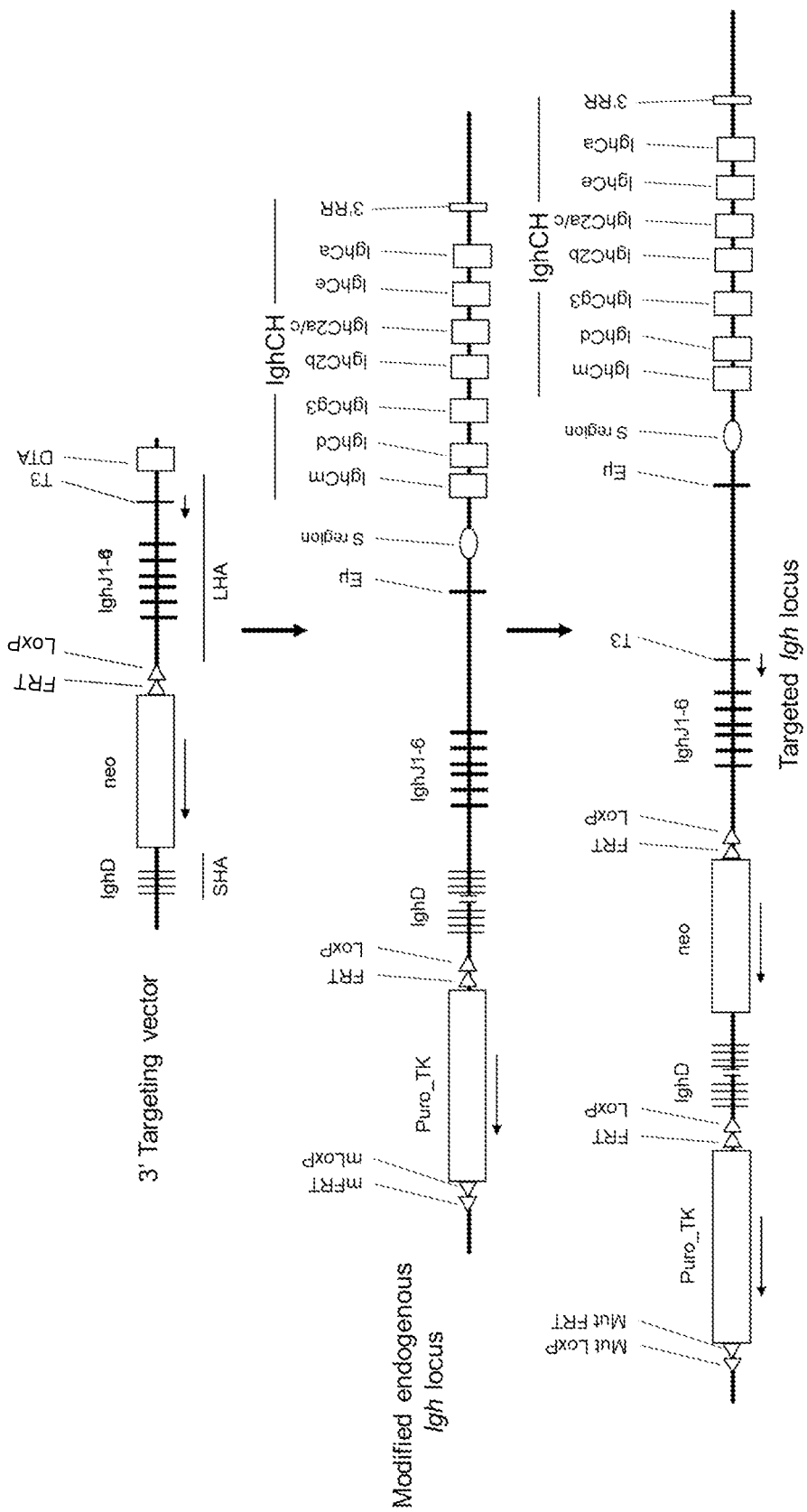
Figure 6:
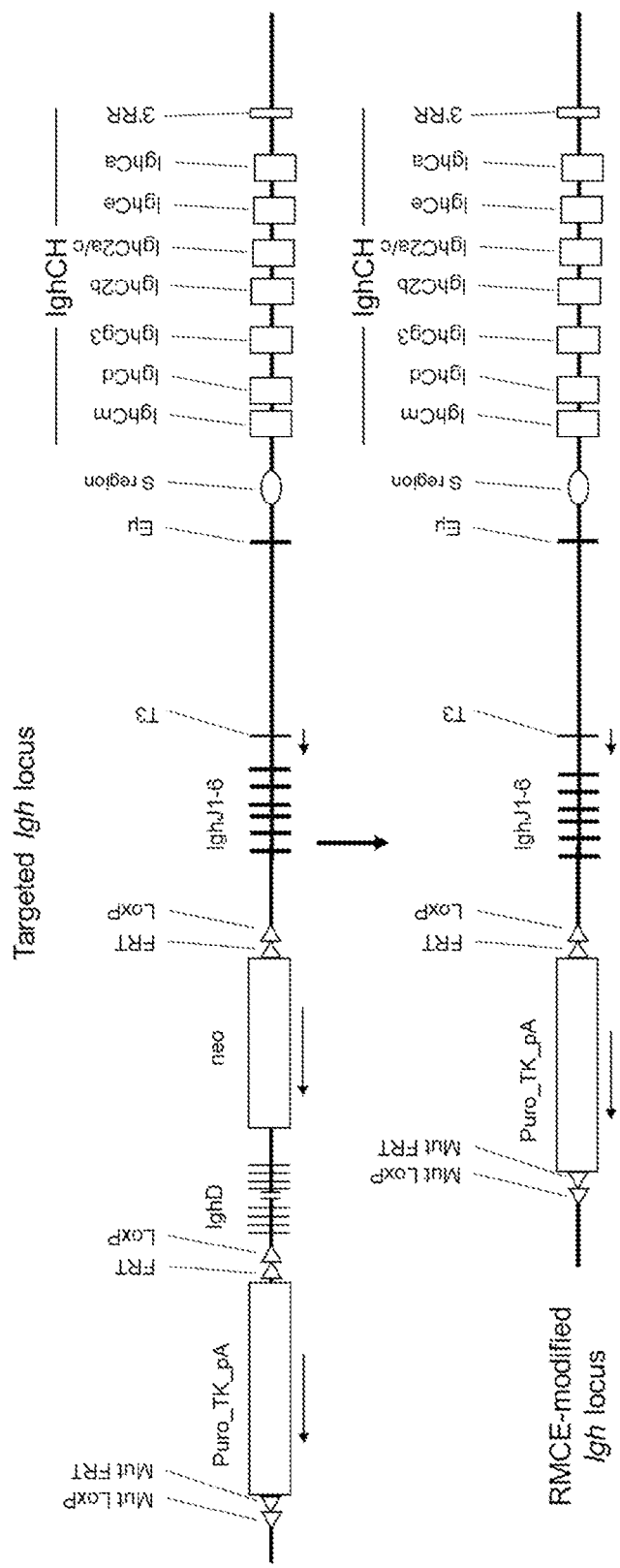
Figure 7:
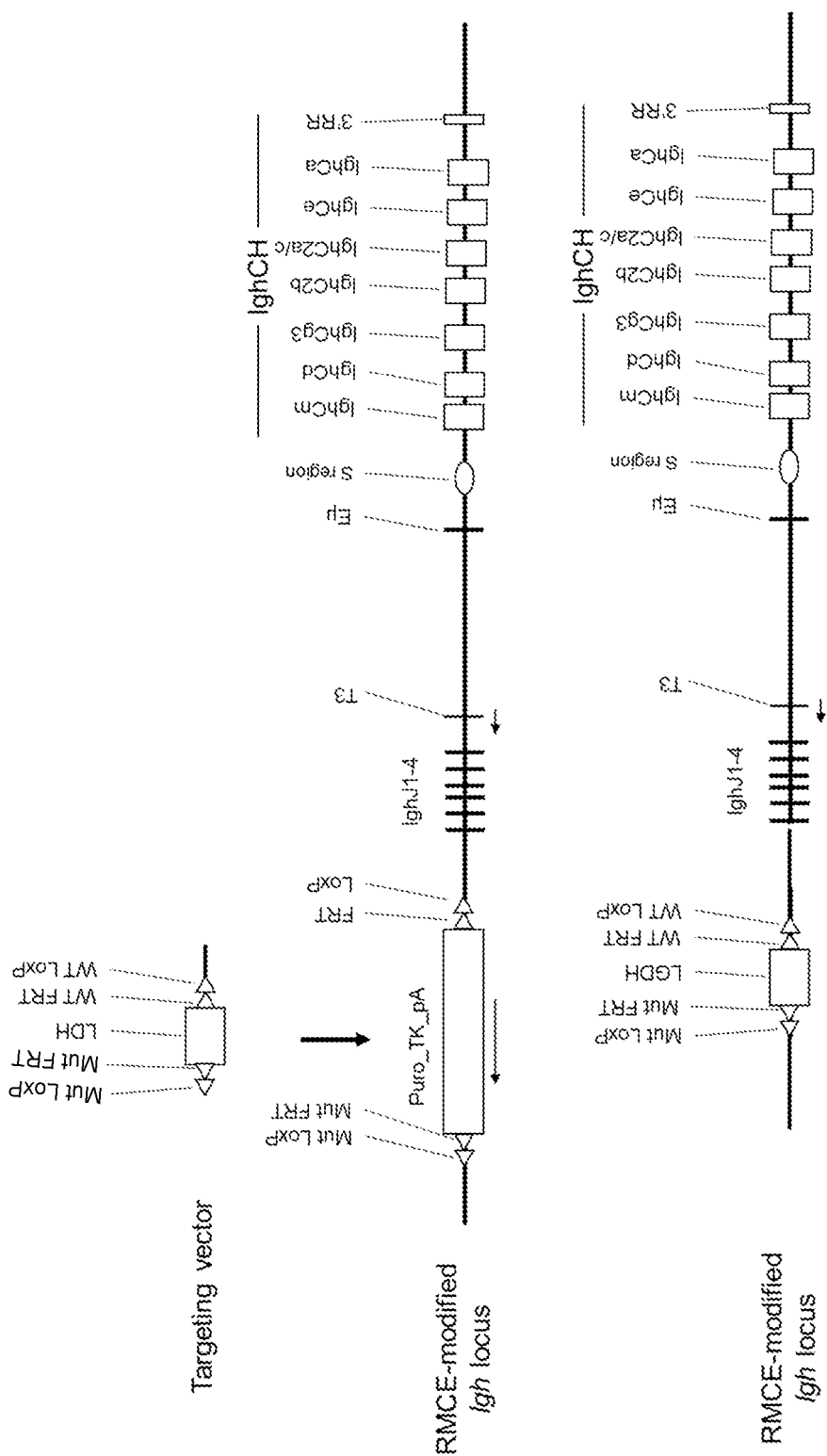

FIGS. 4-7: Strategy for deletion of the endogenous heavy chain DH locus and replacing it with a modified DH locus containing the LDH gene cassette described herein by recombinase-mediated cassette exchange (RMCE) for the production of LHCDR3 Abs. Deletion of the endogenous heavy chain DH locus is done by insertion of appropriate targeting sequences upstream of IGHD1-1, the most JH-distal DH gene segment (FIG. 4) and downstream of IGHD7-27, the most JH-proximal DH gene segment (FIG. 5), followed by in vitro Cre-mediated deletion of the intervening genomic region, resulting in an allele in which the DH locus is replaced by a recombinase-mediated cassette exchange (RMCE) targeting site (FIG. 6). The structure of the RMCE targeting vector containing the LDH gene cassette, the RMCE-modified Igh locus and the resulting targeted Igh locus are depicted in FIG. 7.

Figure 8:
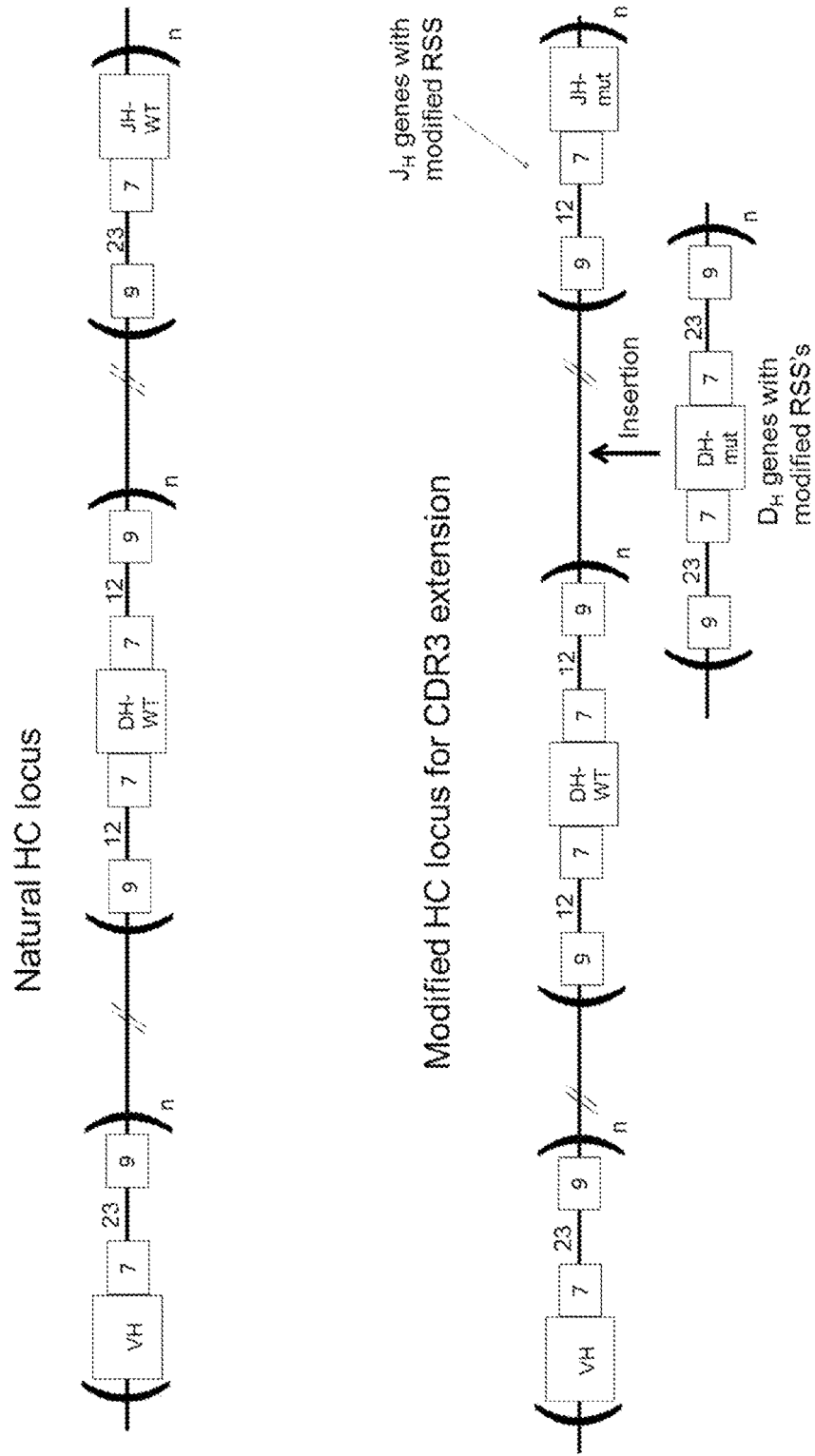

FIG. 8: A strategy to modify the Igh locus recombination signal sequences to promote D to D recombination during VDJ recombination. Top: The natural IgH locus with multiple VH, DH and JH gene segments flanked by 23 bp, 12 bp and 23 bp RSS, respectively. Bottom: The endogenous JH gene segments (JH-WT) are replaced with mutant JH gene segments (JH-mut) that have a 23 bp RSS. A DH minilocus containing native human DH gene segments or the various extended DH gene segments described herein is synthesized to contain flanking 23 bp RSS (DH-mut) and inserted into DH locus as depicted in the figure.

FIG. 9: Tables of DNA sequences (lower case indicates mutated residues)

Table 1 shows mutated bovine long DH gene segments, IGHDS2 and DH3.1.

Table 2 shows a series of human DH gene sequences that have been in silico fused so as to encode long HCDR3 regions. These have also been mutated to any remove stop codons in RF 1, 2, and 3 of the respective native DH gene segments to increase potential antibody diversity.

Table 3 shows a series of human DH gene sequences used to encode long HCDR3 regions in normal human B cells. These have been mutated to any remove stop codons in RF 1, 2, and 3 of the respective native DH gene segments to increase potential antibody diversity.

Table 4 shows long HCDR3 sequences extracted from the IMGT and NCBI databases of expressed Igh cDNAs. These sequences include the N1-DH-N2 portion of the HCDR3 but not the sequences contributed by the 3' part of the VH or the 5' part of the JH and are referred to as SynDH herein (see FIG. 3).

DETAILED DESCRIPTION OF THE INVENTION

Unless indicated or defined otherwise, all terms used herein have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Janeway et al, "Immunobiology" (5th Ed., or more recent editions), Garland Science, New York, 2001.

Unless indicated or defined otherwise, the position of an amino acid residue in an antibody as referred to herein is understood as a position corresponding to the Kabat numbering. The Kabat numbering refers to the numbering of a naturally occurring antibody. An explanation of the Kabat numbering scheme can be found in Kabat, E A, et al., Sequences of proteins of immunological interest. NIH publication no. 91-3242, $5^{th}$ edition (1991).

The LDH expression cassette, locus, and antibody constructs comprising the long HCDR3, such as LHCDR3 Ab described herein, are artificial constructs which are not naturally-occurring. It is well understood that the materials, methods and uses of the invention, e.g., specifically referring to isolated nucleic acid sequences, amino acid sequences, expression constructs, transformed host cells, transgenic animals and recombinant antibodies, are "man-made" or synthetic, and are therefore not considered as a result of the "laws of nature".

The term "antibody" as used herein shall refer to polypeptides or proteins that consist of or comprise antibody domains in various combinations or constructions, which are understood as constant and/or variable domains of the heavy and/or light chains of immunoglobulins, with or without linker sequences. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g., to modify the antigen binding properties or any other property, such as stability or functional properties, such as binding to the Fc receptors.

Herein, the term "antibody" and "immunoglobulin" are used interchangeably.

The term "antibody" as used herein shall particularly refer to antibody constructs comprising VH as a dimer with a VL, thereby obtaining an antigen-binding site comprising VH/VL, or VH as a single variable antibody domain, in combination with constant antibody domains with one or more linking sequence(s) or hinge region(s), such as full-length antibodies or heavy-chain antibodies, composed of one or two single chains, wherein each single chain comprises or consists of a variable heavy chain region (or VH) linked to constant domains. Exemplary antibodies comprise or consist of any of the LHCDR3 Abs further described herein. Antibodies described herein may comprise or consist of antibody domains which are of an IgG type (e.g., an IgG1, IgG2, IgG3, or IgG4 subtype), IgA1, IgA2, IgD, IgE, or IgM type, or their murine counterparts.

In accordance therewith, an antibody is typically understood as a protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively.

In a typical IgG antibody structure, HC or LC each contains at least two domains connected to each other to produce a pair of binding site domains.

The HC of an antibody may comprise a hinge region connecting one or two antigen-binding arms of the antibody to an Fc part. Exemplary antibody constructs may contain antibody constant domains, such as of an Fc connected through the hinge region.

The hinge region may be a naturally-occurring heavy chain hinge region of an immunoglobulin, e.g., of an IgG1 or an IgG3, or an artificial hinge region comprising or consisting of a number of consecutive amino acids which is of about the same length (+/−20%, or +/−10%) as a naturally-occurring one. Preferred hinge regions comprise one or more, e.g., 2, 3, or 4 cysteine residues which may form disulphide bridges to another hinge region thereby obtaining a dimeric construct.

The term "antigen-binding site" or "binding site" refers to the part of an antibody that participates in antigen binding. The antigen binding site in a natural antibody is formed by amino acid residues of the N-terminal variable ("V") regions of the heavy ("H") and/or light ("L") chains, or the variable domains thereof. Three highly variable stretches within the V regions of a heavy chain (and optionally a light chain), referred to as "hypervariable regions", are interposed between more conserved flanking stretches known as framework regions. The antigen-binding site provides for a surface that is complementary to the three-dimensional surface of a bound epitope or antigen, and the hypervariable regions are referred to as "complementarity-determining regions" or "CDRs."

The term "CDR region" or respective sequences refers to the variable antigen-binding region of a variable antibody domain, which includes varying structures capable of binding interactions with antigens. Antibody domains with CDR regions can be used as such or integrated within a larger proteinaceous construct, thereby forming a specific region of such construct with binding function. The varying structures can be derived from natural repertoires of binding proteins such as immunoglobulins, specifically from antibodies or immunoglobulin-like molecules. The varying structures can as well be produced by randomisation techniques, in particular those described herein. These include mutagenized CDR loop regions of antibody variable domains, in particular CDR loops of immunoglobulins.

Typically, an antibody having an antigen-binding site with a specific CDR structure is able to specifically bind a target antigen, i.e., specifically recognizing such target antigen through the CDR loops of a pair of VH/VL domains.

In a LHCDR3 Ab, the antigen-binding site is typically characterized by a specific CDR structure consisting of the VH-CDR1, VH-CDR2, and VH-CDR3 loops optionally together with VL-CDR1, VL-CDR2, and VL-CDR3 loops. The essential difference between conventional and LHCDR3 Ab is the increased length of the VH-CDR3 loop, although the sequence will often also vary, which is placed at the center of the antigen binding site. In a heavy chain-only version of a LHCDR3 Ab, there are no VL-CDR1, VL-CDR2, or VL-CDR3 loops. In such case, all antigen binding activity is provided by the VH-CDR loops, primarily determined by the VH-CDR3 loop, which extends out furthest from the antigen-binding site due to its increased length. In both scenarios, the antigen-binding site is understood to be native, or of a native structure and/or conformation, if produced by an animal, e.g., a transgenic non-human animal as described herein. Though the antigen-binding site can be artificially produced, because engineered by recombination techniques synthesizing new structures, the incorporation of respective genes encoding the respective antibody into a transgenic non-human animal results in the production of new synthetic antibodies which have a native conformation. Still, the LHCDR3 Ab is understood as an artificial product that is not naturally-occurring other than in the host organisms described herein.

Such native antibody conformation can be further affinity matured by any in vivo or in vitro technique of affinity maturation, thereby producing polyclonal and/or monoclonal antibodies comprising an artificial antigen-binding site characterized by a native conformation, and further characterized by a high affinity of specifically binding its target antigen.

The term "antibody" shall apply to antibodies of animal origin, including human species, such as mammalian, including human, murine, rabbit, rat, or avian, such as chicken, which term shall particularly include recombinant antibodies that are based on a sequence of animal origin, e.g., mouse sequences.

The term "antibody" further applies to fully human antibodies.

The term "fully human" as used with respect to an immunoglobulin, is understood to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin or antibody libraries or from animals transgenic for one or more human immunoglobulin.

A human immunoglobulin is preferably selected or derived from the group consisting of IgA1, IgA2, IgD, IgE, IgG1, IgG2, IgG3, IgG4 and IgM.

A murine immunoglobulin is preferably selected or derived from the group consisting of IgA, IgD, IgE, IgG1, IgG2a, IgG2b, IgG2c, IgG3 and IgM.

The term "antibody" further applies to chimeric antibodies, with mixed sequences that originate from different species, such as sequences of murine and human origin.

Specifically, the term "antibody" applies to antibodies produced by transgenic non-human animals, e.g., from mice, which comprise human antigen-binding regions and non-human (e.g., murine) constant regions or framework sequences.

The term "chimeric" as used with respect to an immunoglobulin or an antibody refers to those molecules wherein one portion of an antibody chain is homologous to corresponding sequences in immunoglobulins derived from a particular species or belonging to a particular class, while the remaining segment of the chain is homologous to corresponding sequences in another species or class. Typically, the variable region mimics the variable regions of immunoglobulins derived from one species of mammals, while the constant portions are homologous to sequences of immunoglobulins derived from another. For example, the variable region can be derived from presently known sources using readily available B-cells from human host organisms in combination with constant regions derived from, for example, non-human cell preparations.

The term "antibody" further applies to a monoclonal antibody, specifically a recombinant antibody, which term includes all types of antibodies and antibody structures that are prepared, expressed, created or isolated by recombinant means, such as antibodies originating from animals, e.g., mammalians including human, that comprises genes or sequences from different origin, e.g., chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

The term "antibody" is understood to include functionally active variants of new or existing (herein referred to as "parent"), e.g., naturally occurring immunoglobulins. It is further understood that the term includes antibody variants, and shall also include derivatives of such molecules as well. A derivative is any combination of one or more antibodies and or a fusion protein in which any domain of the antibody, e.g., an antibody domain comprising the antigen-binding site of the VH domain, or the VH domain, which may be fused at any position to one or more other proteins, such as to other antibodies, e.g., a binding structure comprising CDR loops, a receptor polypeptide, but also to other ligands, enzymes, toxins and the like. The antibodies as described herein can be specifically used as isolated polypeptides or as combination molecules, e.g., through recombination, fusion or conjugation techniques, with other peptides or polypeptides.

A derivative of the antibody may also be obtained by association or binding to other substances by various chemical techniques such as covalent coupling, electrostatic interaction, disulphide bonding, etc. The other substances bound to the antibodies may be lipids, carbohydrates, nucleic acids, organic and inorganic molecules or any combination thereof (e.g., PEG, prodrugs or drugs). A derivative may also comprise an antibody with the same amino acid sequence but made completely or partly from non-natural or chemically modified amino acids. In a specific embodiment, the antibody is a derivative comprising an additional tag allowing specific interaction with a biologically acceptable compound. There is not a specific limitation with respect to the tag usable in the present invention, as far as it has no or tolerable negative impact on the binding of the immunoglobulin to its target. Examples of suitable tags include His-tag, Myc-tag, FLAG-tag, Strep-tag, Calmodulin-tag, GST-tag, MBP-tag, and S-tag. In another specific embodiment, the antibody is a derivative comprising a label. The term "label" as used herein refers to a detectable compound or composition which is conjugated directly or indirectly to the antibody so as to generate a "labeled" antibody. The label may be detectable by itself, e.g., radioisotope labels or fluorescent labels, or, in the case of an enzymatic label, may catalyze chemical alteration of a substrate compound or composition which is detectable.

A derivative of an antibody is e.g., derived from a parent antibody or antibody sequence, such as a parent antigen-binding (e.g., CDR) or framework (FR) sequence, e.g., mutants or variants obtained by e.g., in silico or recombinant engineering or else by chemical derivatization or synthesis.

The term "variant" shall specifically encompass functionally active variants. The functional variants of an antibody as described herein are particularly functional with regard to the specificity of antigen-binding.

The term "variant" shall particularly refer to antibodies, such as mutant antibodies or fragments of antibodies, e.g., obtained by mutagenesis methods, in particular to delete, exchange, introduce inserts or deletions into a specific antibody amino acid sequence or region or chemically derivatize an amino acid sequence, e.g., in the constant domains to engineer improved antibody stability, enhanced effector function or half-life, or in the variable domains to modulate antigen-binding properties, e.g., by affinity maturation techniques available in the art. Any of the known mutagenesis methods may be employed, including point mutations at desired positions, e.g., obtained by randomization techniques, or domain deletion or fusion, as used for LHCDR3 Ab engineering. In some cases, positions are chosen randomly, e.g., with either any of the possible amino acids or a selection of preferred amino acids to randomize the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The functional activity of an antibody in terms of antigen-binding is typically determined in an ELISA assay, BIAcore assay, Octet BLI assay, or FACS based assay when the antigen is expressed on a cell surface or intracellularly.

Functionally active variants may be obtained, e.g., by changing the sequence of a parent antibody, e.g., a monoclonal antibody having a specific native structure of an immunoglobulin, such as an IgG1 structure, to obtain a variant having the same specificity in recognizing a target antigen, but having a structure which differs from the parent structure, e.g., to modify any of the antibody domains to introduce specific mutations, or to produce a fragment of the parent molecule.

Specific functionally active variants comprise one or more functionally active CDR variants or a parent antibody, each of which comprises at least one point mutation in the parent CDR sequence, and comprises or consists of the amino acid sequence that has at least 60% sequence identity with the parent CDR sequence, preferably at least 70%, at least 80%, at least 90% sequence identity.

A specific variant is e.g., a functionally active variant of the parent antibody, wherein the parent CDR sequences are incorporated into human framework sequences, wherein optionally 1, 2, 3, or 4 amino acid residues of each of the parent CDR sequences may be further mutated by introducing point mutations to improve the stability, specificity and affinity of the parent or humanized antibody.

Specifically, the antibody may comprise a functionally active CDR variant of any of the CDR sequences of a parent antibody, wherein the functionally active CDR variant comprises at least one of
   a) 1, 2, or 3 point mutations in the parent CDR sequence; and/or
   b) 1 or 2 point mutations in any of the four C-terminal or four N-terminal, or four centric amino acid positions of the parent CDR sequence; and/or
   c) at least 60% sequence identity with the parent CDR sequence;
preferably wherein the functionally active variant antibody comprises at least one of the functionally active CDR variants as described herein. Specifically, the functionally active variant antibody comprising one or more of the functionally active CDR variants has a specificity to bind the same epitope as the parent antibody.

According to a specific aspect, a point mutation is any mutation which is or results in an amino acid substitution, deletion and/or insertion of one single amino acid, or more than one (typically only a few) amino acids in series e.g., 2, 3, or 4 amino acids in series.

"Percent (%) amino acid sequence identity" with respect to antibody sequences is defined as the percentage of amino acid residues in a candidate sequence that are identical with the amino acid residues in the specific polypeptide sequence, after aligning the sequence and introducing gaps according to methods well known in the art, such as CLUSTALW (Chenna R, Sugawara H, Koike T, Lopez R, Gibson T J, Higgins D G, Thompson. J D. (2003). Multiple sequence alignment with the Clustal series of programs. Nucleic Acids Res., 31, 3497-3500), if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

An antibody variant is specifically understood to include homologs, analogs, fragments, modifications or variants with a specific glycosylation pattern, e.g., produced by glycoengineering, which are functional and may serve as functional equivalents, e.g., binding to the specific targets and with functional properties. An antibody may be glycosylated or unglycosylated. For example, a recombinant antibody as described herein may be expressed in an appropriate mammalian cell to allow a specific glycosylation of the molecule as determined by the host cell expressing the antibody.

The term "beta sheet" or "beta strand" of an antibody domain, in particular of a constant antibody domain, is herein understood in the following way. An antibody domain typically consists of at least two beta strands connected laterally by at least two or three backbone hydrogen bonds, forming a generally twisted, pleated sheet. A beta strand is a single continuous stretch of amino acids of typically 3 to 10 amino acids length adopting such an extended conformation and involved in backbone hydrogen bonds to at least one other strand, so that they form a beta sheet. In the beta sheet, the majority of beta strands are arranged adjacent to other strands and form an extensive hydrogen bond network with their neighbors in which the N—H groups in the backbone of one strand establish hydrogen bonds with the C=O groups in the backbone of the adjacent strands.

The structure of antibody constant domains, such as a Cκ, CH1, CH2 or CH3 domain, is similar to that of variable domains, consisting of beta-strands connected by loops, some of which contain short alpha-helical stretches. The framework is mostly rigid and the loops are comparatively more flexible, as can be seen from the x-ray crystallographic b-factors of various Fc crystal structures. An antibody constant domain typically has seven beta strands forming a beta-sheet (A-B-C-D-E-F-G), wherein the beta strands are linked via loops, three loops being located at the N-terminal tip of the domain (A-B, C-D, E-F), and further three loops being located at the N-terminal tip of the domain (B-C, D-E, F-G). A "loop region" of a domain refers to the portion of the protein located between regions of beta strands (for example, each CH3 domain comprises seven beta sheets, A to G, oriented from the N- to C-terminus).

In certain embodiments, antibody domains may comprise mutations, e.g., can have at least a portion of one or more beta strands replaced with heterologous sequences, such as to include mutations which facilitate pairing with another domain, e.g., interdomain disulfide bridges, such as connecting beta-sheet regions of two antibody domains, knob and/or hole mutations, or strand-exchange.

Specific domain mutations can include the incorporation of new (additional) amino acid residues, e.g., Cys residues, which are capable of forming additional interdomain or interchain disulfide bridges to stabilize
a) an antibody domain by an additional intradomain disulfide bonds, and/or
b) a domain pair by an interdomain disulfide bridge between a Cκ domain and a CH1 domain,
c) two chains of antibody domains by additional interchain disulfide bridging.

Disulfide bonds are usually formed from the oxidation of thiol groups of two cysteines or other thiol forming amino acids or amino acid analogues to form artificial disulfide bridges by linking the S-atoms of the amino acid side chains. Specifically, cysteine may be inserted (by an additional amino acid or an amino acid substitution) between a pair of domains that warrant the additional cysteine modifications to thereby produce a stabilized domain pair by disulfide bond formation.

A "pair" of antibody domains is understood as a set of two antibody domains in a certain arrangement, wherein one has an area on its surface or in a cavity that it specifically binds to, and is therefore complementary to an area on the other one. Antibody domains may associate to form a pair of domains through contact of a beta-sheet region. Such domain pair is also referred to as a (hetero- or homo-) dimer, which is e.g., associated by electrostatic interaction, recombinant fusion or covalent linkage, placing two domains in direct physical association, e.g., including both in solid and in liquid form.

The term "cognate" with respect to a pair of associated domains or domain dimers is understood as domains, each of which has a mutually complementary binding interface to create an interdomain contact surface on each of the domains. Upon contacting each other, the pair of domains is formed through association of these contact surfaces.

Antibodies may be produced by first screening the antigen-binding sites formed by folding the CDR sequences in each binding site of an antibody library, to select specific binders. As a next step, the selected library members may serve as a source of CDR sequences (or parent CDR sequences, which may be further modified to modulate the antigen binding and even phenotypic properties) which may be used to engineer any kind of antibody constructs, e.g., full-length immunoglobulins or antigen-binding fragments thereof.

A library of antibodies (such as comprising a repertoire of specific antibody constructs recognizing the same target antigen, or a naïve library of antibodies which is produced by a certain animal or breed, e.g., the transgenic non-human animal described herein, which library comprises a repertoire of antibodies recognizing different target antigens) refers to a set or a collection of antibodies (e.g., LHCDR3 Abs described herein), each antibody being displayed appropriately in the chosen display system or containments.

Specific display systems couple a given protein, herein the antibody, e.g., LHCDR3 Abs described herein, with its encoding nucleic acid, e.g., its encoding mRNA, cDNA or genes. Thus, each member of a library comprises a nucleic acid encoding the antibody which is displayed thereon. Display systems encompass, without being limited to, cells, virus such as phages, ribosomes, eukaryotic cells such as yeast, DNAs including plasmids, and mRNA display.

Any antibody gene diversity library may be used for such purposes, which, e.g., includes a high number of individual library members, to create a diversity of antibody sequences, or employing preselected libraries, which are e.g., enriched in stabilized or functionally active library members. For example, a display system can be enriched in library members that bind to a certain target.

Libraries can be constructed by well-known techniques, involving, for example, chain-shuffling methods. For heavy chain shuffling, the antibodies are cloned into a vector containing a human VH gene repertoire to create phage antibody library transformants. Further methods involve site-directed mutagenesis of CDRs of the antibodies, or CDR randomization where partial or entire CDRs are randomized, using either total randomization of targeted residues with the application of NNK codon-containing mutagenic oligonucleotides, or partial randomization of the targeted residues using parsimonious mutagenesis, where the oligonucleotides at positions encoding for targeted amino acid residues contain a mixture biased towards the original nucleotide base. Alternatively, the library can be constructed using error-prone PCR, with the application of dNTP analogs, error-prone polymerase, or the addition of $Mn^{2+}$ ions in the PCR reaction.

Various techniques are available for the manufacture of genes encoding the designs of human antibody library construction. It is possible to produce the DNA by a completely synthetic approach, in which the sequence is divided into overlapping fragments which are subsequently prepared as synthetic oligonucleotides These oligonucleotides are mixed together, and annealed to each other by first heating to ca. 100° C. and then slowly cooling down to ambient temperature. After this annealing step, the synthetically assembled gene can be either cloned directly, or it can be amplified by PCR prior to cloning. This is particularly desirable when a large single-pot human library is desirable and enormous resources are available for the construction process.

Specific methods employ phage, phagemid and/or yeast libraries for direct binder selection and internalizing phage antibody selection. Further methods for site directed mutagenesis can be employed for generation of the library insert, such as the Kunkel method (Kunkel T A. Rapid and efficient site-specific mutagenesis without phenotypic selection. Proc Natl Acad Sci USA. 1985 January; 82(2):488-92) or the Dpnl method [Weiner M P, Costa G L, Schoettlin W, Cline J, Mathur E, Bauer J C. Site-directed mutagenesis of double-stranded DNA by the polymerase chain reaction. *Gene* 151(1-2):119-23(1994 Dec. 30)].

A "naïve library" refers to a library of polynucleotides (or polypeptides encoded by such polynucleotides) that has not been interrogated for the presence of antibodies having specificity to a particular antigen. A "naïve library" also refers to a library that is not restricted to, or otherwise biased or enriched for, antibody sequences having specificity for any group of antigens, or for a particular antigen. A naïve library is thus distinct from a "maturation library" (such as, for example, an "affinity maturation library").

A naïve library may also comprise a "preimmune" library, which refers to a library that has sequence diversity similar to naturally-occurring antibody sequences before such naturally occurring sequences have undergone antigen selection. Such preimmune libraries may be designed and prepared so as to reflect or mimic the pre-immune repertoire, and/or may be designed and prepared based on rational design informed by the collection of V, D, and J genes, and other large databases of heavy chain sequences (e.g., publicly known germline sequences). In certain embodiments of the invention, cassettes representing the possible V, D, and J diversity found in the human or non-human repertoire, as well as junctional diversity (i.e., N1 and N2), are synthesized de novo as single or double-stranded DNA oligonucleotides.

A "maturation library" refers to a library that is designed to enhance or improve at least one characteristic of an antibody sequence that is identified upon interrogation of a library, such as a naïve library or a preimmune library, for the presence of antibody sequences having specificity for the antigen. Such maturation libraries may be generated by incorporating nucleic acid sequences corresponding to: one or more CDRs; one or more antigen binding regions; one or more VH regions; and/or one or more heavy chains; obtained from or identified in an interrogation of a naïve library into libraries designed to further mutagenize in vitro or in vivo to generate libraries with diversity introduced in the context of an initial (parent) antibody.

As a different example of array technology, B-cell cloning can be used that yields genes encoding antibody constructs described herein, at manually or computer-addressable locations in an array of B-cells. Robotics or manual methods can be used to manipulate this array to re-array only cells expressing a certain type of antibodies and/or those which specifically recognize a certain target.

In certain embodiments, B-cell cloning, e.g., from suitably immunized non-human transgenic animals, such as those described herein, which are genetically engineered to produce antibodies, or mammalian cell expression libraries are used, or alternatively a large population of stably transformed mammalian cells are generated by the standard methods and robotic tools of antibody and protein engineering. Individual clones are kept viable in addressable wells arrayed on plates in suitable incubators and/or under long-term storage conditions, e.g., that may comprise freezing cell suspensions in liquid nitrogen with storage at −135 degrees C., or under other acceptable conditions that allow recovery of the stored cell lines.

The term "repertoire" as used herein shall refer to a collection of variants, such as variants characterized by a diversity of target epitope or antigen specificities. Typically, the structure of an antibody (also called "scaffold") is the same in such repertoire, yet with a variety of different CDR sequences.

As is well-known in the art, there is a variety of display and selection technologies that may be used for the identification and isolation of proteins with certain binding characteristics and affinities, including, for example, display technologies such as cellular and non-cellular methods and in particular mobilized display systems. Among the cellular systems, the phage display, virus display, yeast or other eukaryotic cell display, such as mammalian or insect cell display may be used. Mobilized systems relate to display systems in a soluble format, such as in vitro display systems, among them ribosome display, mRNA display or nucleic acid display.

Screening the library for library members displaying an antigen-binding structure able to bind the target may be done by any suitable method. The screening step may comprise one or several rounds of selection (also referred to as panning).

Any screening method suitable for identifying antibodies able to bind the target antigen may be used. In particular, the rounds of selection may comprise incubating the library in the presence of said target, so as to select the antibodies which bind said antigen, or an epitope thereof.

Once antibodies with the desired structure are identified, such antibodies can be produced by methods well-known in the art, including, for example, hybridoma techniques or recombinant DNA technology.

In the hybridoma method, an appropriate non-human host animal, such as a rodent or mouse, is immunized to activate lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell.

Culture medium in which hybridoma cells are growing is assayed for production of monoclonal antibodies directed against the antigen. Preferably, the binding specificity of monoclonal antibodies produced by hybridoma cells is determined by flow cytometry, immunoprecipitation or by an in vitro binding assay, such as an enzyme-linked immunosorbent assay (ELISA).

According to another specific example, recombinant monoclonal antibodies can be produced by isolating the DNA encoding the required antibody chains and transfecting a recombinant host cell with the coding sequences for expression, using well-known recombinant expression vectors, e.g., the plasmids or expression cassette(s) comprising the nucleotide sequences encoding the antibody sequences. Recombinant host cells can be prokaryotic and eukaryotic cells.

According to a specific aspect, the coding nucleotide sequence may be used for genetic manipulation to humanize the antibody or to improve the affinity, or other characteristics of the antibody. For example, the constant region may be engineered to resemble human constant regions. It may be desirable to genetically manipulate the antibody sequence to obtain greater affinity to the target antigen. It will be apparent to one of skill in the art that one or more polynucleotide changes can be made to the antibody and still maintain its binding ability to the target (epitope or antigen).

The production of antibody molecules, by various means, is generally well understood. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

Monoclonal antibodies can e.g., be produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 133: 3001; and Brodeur et al., 1987, Monoclonal Antibody Production Techniques and Applications, (Marcel Dekker, Inc., New York), pp. 51-63).

The term "target" as used herein shall refer to epitopes or antigens.

The term "antigen" as used herein shall in particular include all antigens and target molecules that have been shown to be recognised by a binding site of an antibody (at least one paratope) as a result of exposure of the antigen to the immune system of an animal or to a library of antibodies. Specifically, preferred antigens as targeted by the antibody described herein are those molecules that have already been proven to be or are capable of being immunologically or therapeutically relevant, especially those, for which a clinical efficacy has been tested.

The term "antigen" is used to describe a whole target molecule or a fragment of such molecule, especially sub-structures, e.g., a polypeptide or carbohydrate structure of targets. Such sub-structures which are often referred to as "epitopes", e.g., B-cell epitopes, T-cell epitope), can be immunologically relevant, i.e., are also recognizable by natural or monoclonal antibodies.

The term "epitope" as used herein shall in particular refer to a molecular structure present at the interface between the antigen and a specific antibody wherein the antibody surface of interaction with the epitope is referred to as the "paratope". Chemically, an epitope may be composed of a carbohydrate sequence or structure, a peptide sequence or set of sequences in a discontinuous epitope, a fatty acid or an oligo-or polynucleotide. Where the antigenic molecule is an organic, biochemical or inorganic substance it is referred to as a "hapten". Epitopes or haptens may consist of derivatives or any combinations of the above substances. If an epitope is a polypeptide, it will usually include at least 3 amino acids, preferably 8 to 50 amino acids, and more preferably between about 10-20 amino acids in the peptide. Epitopes can be either linear or discontinuous epitopes. A linear epitope is comprised of a single segment of a primary sequence of a polypeptide or carbohydrate chain. Linear epitopes can be contiguous or overlapping. Discontinuous epitopes are comprised of amino acids or carbohydrates brought together by folding the polypeptide to form a tertiary structure and the amino acids are not necessarily adjacent to one another in the linear sequence. Specifically, epitopes are at least part of diagnostically relevant molecules, i.e., the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e., molecules which can be targeted by the specific binding domain which changes the course of the disease.

As used herein, the term "specificity" or "specific binding" refers to a binding reaction which is determinative of the cognate ligand of interest in a heterogeneous population of molecules. Thus, under designated conditions (e.g., immunoassay conditions), the antibody binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10-fold different than a competing target in the sample, preferably the difference is at least 100-fold, and more preferred a least 1000-fold.

A specific binding does not exclude certain cross-reactivity with similar antigens, or the same antigens of a different species (analogues). For example, a binding entity may also preferably cross-react with rodent targets analogous to human targets, to facilitate preclinical animal studies.

The term "locus" as used herein refers to a DNA coding sequence or segment of DNA that code for an expression product which is a genomic sequence, such as part of a genome of a host organism, or part of a vector, e.g., integrated at a target site, such as defined restriction sites, or regions of homology.

Restriction sites can be designed to ensure insertion of an expression cassette in the proper reading frame. Typically, foreign (herein also referred to as exogenous) DNA is inserted at one or more restriction sites of a vector DNA, and then is carried by the vector into a host cell along with the transmissible vector DNA.

Typically, a locus encompasses at least one gene. The term "locus" does not imply that a gene is actively transcribed or intact. Genes may be encompassed that have been inactivated.

In specific embodiments described herein, the transgenic animal's endogenous kappa and lambda light chain loci are non-functional by one or more modifications, such as loss-of function mutations, or deletion of endogenous light chain loci kappa, or parts thereof.

A locus may be engineered to express exons encoding an antibody, such as further described herein.

In one embodiment, a recombinant locus can be created using various conventional techniques for site-specific editing and/or recombination. Preferably, a modified locus is generated by inserting a piece of DNA (referred to here as the "donor DNA") containing gene segments encoding, e.g., long DH segments, into a modified version of a non-human animal immunoglobulin locus such as a heavy chain locus of a host organism (referred to here as the "acceptor allele"). The acceptor allele may contain recognition sites for a site-specific DNA recombinase, such as the Cre recombinase (a loxP site and a mutated version of the loxP site). The donor DNA may be flanked by the same Cre recombinase recognition sites (at both, the 5'-end and the 3'-end, e.g., on one side there is a loxP site and on the other there will be a mutated version of the loxP site). The Cre recombinase may be used to catalyze the insertion of the donor DNA into the acceptor allele.

The term "targeting sequence" refers to a sequence that is homologous to DNA sequences in the genome of a cell that flank or occur adjacent to the region of an immunoglobulin genetic locus that is to be modified. The flanking or adjacent sequence may be within the locus itself or upstream or downstream of coding sequences in the genome of the host cell. Targeting sequences are inserted into recombinant DNA vectors for use in cell transfections such that sequences to be inserted into the cell genome, such as the sequence of a recombination site, are flanked by the targeting sequences of the vector.

In many instances in which homologous recombination is employed to accomplish a genetic change in a genome (such as an insertion or a deletion) a further modification would involve the use of engineered site-specific endonucleases to increase the likelihood that a desired outcome can be accomplished. Such endonucleases are of value because they can be engineered to be highly specific for unique sequences in a target genome, and because they cause double-stranded DNA breaks at the sites they recognize. Double-stranded breaks promote homologous recombination with targeting vectors that carry targeting homology with DNA in the immediate vicinity of the breaks. Thus, the combination of a targeting vector and a site-specific endonuclease that cleaves DNA within or close to the region targeted by a vector typically results in much higher homologous recombination efficiency than use of a targeting vector alone. Furthermore, it is possible to facilitate the creation of a genomic deletion through use of one or more site-specific endonucleases and a targeting vector comprised of two targeting homology arms in which one arm targets one side of the region to be deleted and the other arm targets the other side.

Site-specific recombination differs from general homologous recombination in that short specific DNA sequences, which are required for the recombinase recognition, are the only sites at which recombination occurs. Site-specific recombination requires specialized recombinases to recognize the sites and catalyze the recombination at these sites. A number of bacteriophage and yeast-derived site-specific recombination systems, each comprising a recombinase and specific cognate target sites, have been shown to work in eukaryotic cells for the purpose of DNA integration and are therefore applicable for use as described herein. These include the bacteriophage P1 Cre/lox, yeast FLP-FRT system, and the Dre system of the tyrosine family of site-specific recombinases. Such systems and methods of use are well-described in the prior art. The recombinase-mediated cassette exchange (RMCE) procedure is facilitated by usage of the combination of wild-type and mutant loxP (or FRT, etc.) sites together with the appropriate recombinase (e.g., Cre or Flp), and negative and/or positive selection. RMCE will occur when the sites employed are identical to one another and/or in the absence of selection, but the efficiency of the process is reduced because excision rather than insertion reactions are favored, and (without incorporating positive selection) there will be no enrichment for appropriately mutated cells.

Other systems of the tyrosine family such as bacteriophage lambda Int integrase, HK2022 integrase, and in addition systems belonging to the separate serine family of recombinases such as bacteriophage phiC31, R4Tp901 integrases are known to work in mammalian cells using their respective recombination sites, and are also applicable for use as described herein.

The methods described herein specifically utilize site-specific recombination sites that utilize the same recombinase, but which do not facilitate recombination between the sites. For example, a loxP site and a mutated loxP site can be integrated into the genome of a host, but introduction of Cre into the host will not cause the two sites to undergo recombination; rather, the loxP site will recombine with another loxP site, and the mutated site will only recombine with another likewise mutated loxP site.

Two classes of variant recombinase sites are available to facilitate recombinase-mediated cassette exchange. One harbors mutations within the 8 bp spacer region of the site, while the other has mutations in the 13-bp inverted repeats.

Spacer mutants such as lox511 (Hoess, et al., Nucleic Acids Res., 14:2287-00 (1986)), lox5171 and lox2272 (Lee and Saito, Gene, 216:55-65 (1998)), m2, m3, m7, and mil (Langer, et al., Nucleic Acids Res., 30:3067-77 (2002)) recombine readily with themselves but have a markedly reduced rate of recombination with the wild-type site. Examples of the use of mutant sites of this sort for DNA insertion by recombinase-mediated cassette exchange can be found in Baer and Bode, Curr Opin Biotechnol, 12:473-80 (2001.

Inverted repeat mutants represent a second class of variant recombinase sites. For example, loxP sites can contain altered bases in the left inverted repeat (LE mutant) or the right inverted repeat (RE mutant). An LE mutant, lox71, has 5 bp on the 5' end of the left inverted repeat that is changed from the wild type sequence to TACCG (Araki, Nucleic Acids Res., 25:868-72 (1997)). Similarly, the RE mutant, lox66, has the five 3'-most bases changed to CGGTA. Inverted repeat mutants can be used for integrating plasmid inserts into chromosomal DNA. For example, the LE mutant can be used as the "target" chromosomal loxP site into which the "donor" RE mutant recombines. After recombination, a donor piece of DNA that contained an RE site will be found inserted in the genome flanked on side by a double mutant site (containing both the LE and RE inverted repeat mutations) and on the other by a wild-type site (Lee and Sadowski, Prog Nucleic Acid Res Mol Biol., 80: 1-42 (2005)). The double mutant is sufficiently different from the wild-type site that it is unrecognized by Cre recombinase and the inserted segment therefore cannot be excised by Cre-mediated recombination between the two sites.

In certain aspects, site-specific recombination sites can be introduced into introns or intergenic regions, as opposed to coding nucleic acid regions or regulatory sequences. This may avoid inadvertently disrupting any regulatory sequences or coding regions necessary for proper gene expression upon insertion of site-specific recombination sites into the genome of the animal cell.

Introduction of the site-specific recombination sites may be achieved by conventional homologous recombination techniques. Such techniques are described in references such as e.g., Sambrook and Russell (2001) *Molecular cloning: a laboratory manual*, 3d ed. (Cold Spring Harbor, N.Y.: Cold Spring Harbor Laboratory Press); Nagy, (2003) *Manipulating the mouse embryo: a laboratory manual*, 3d ed. (Cold Spring Harbor, N.Y.: Cold Spring Harbor Laboratory Press); and Miller, Vandome, and McBrewster (2009) *Genetic Recombination: Nucleic acid, Homology (biology), Homologous recombination, Non-homologous end joining, DNA repair, Bacteria, Eukaryote, Meiosis, Adaptive immune system, V(D)J recombination.*

Specific recombination into the genome can be facilitated using vectors designed for positive or negative selection as known in the art. In order to facilitate identification of cells that have undergone the replacement reaction, an appropriate genetic marker system may be employed and cells selected by, for example, use of a selection medium. However, in order to ensure that the genome sequence is substantially free of extraneous nucleic acid sequences at or adjacent to the two end points of the replacement interval, desirably the marker system/gene can be removed following selection of the cells containing the replaced nucleic acid.

The recombinase may be provided as a purified protein, or may be expressed from a construct transiently expressed within the cell in order to provide the recombinase activity. Alternatively, the cell may be used to generate a transgenic animal, which may be crossed with an animal that expresses said recombinase, in order to produce progeny that lack the marker gene and associated recombination sites.

Herein, the term "heterologous" with reference to a gene, gene segment, or locus, indicates that the gene, gene segment, and locus, respectively, is not native to a cell (i.e., not natively occurring in a wild-type cell of the same species at the same location within the cellular genome), or foreign to a cell to produce a recombinant cell, i.e., the gene, gene segment, or locus is present in the genome of a modified (recombinant) cell which is not a wild-type cell. A heterologous gene segment may be a wild type gene segment present at a locus which is different from the respective locus in a wild type cell (thus not found in nature at the same locus). A heterologous gene segment may be a (modified or unmodified) endogenous gene if it is present at a different locus in the genome other than found in a wild type gene or organism. An example of such heterologous gene, gene segment, or locus is a modified endogenous one, such as a construct comprising an LGDH expression construct described herein, wherein at least one DH gene segment is modified e.g., to produce a 23 bp spacer in a RSS sequence of said DH gene segment, or to delete one or more stop codons of said DH gene segment, or to link and/or fuse said DH segment to one or more further DH gene segments, optionally using one or more heterologous ("foreign") intergenic regions.

Herein the term "endogenous" with reference to a gene, gene segment, or locus, indicates that the gene, gene segment, and locus, respectively, is native to a cell, i.e., the gene, gene segment, or locus is present at a particular locus in the genome of a non-modified cell. An endogenous gene segment may be a wild type gene segment present at that locus in a wild type cell (as found in nature). According to a specific example, an endogenous gene, gene segment, or locus is modified by deleting a nucleotide sequence, or by inserting a foreign (heterologous) nucleotide sequence, thereby producing an artificial construct.

In specific embodiments, gene segments are introduced into an immunoglobulin locus, e.g., by a CRISPR/Cas9 technology using a non-homologous end joining approach (see He, et al, Nuc. Acids Res., 44:e85, 2016) rather than homology directed repair.

The term "expression cassette" as described herein refers to nucleic acid molecules or genetic constructs containing a desired coding sequence sequences in operable linkage, so that hosts comprising such expression cassette are capable of producing the encoded proteins. The expression system may be included in a vector to transform a host; however, the relevant coding sequence may also be directly integrated into the host chromosome.

The LDH expression cassette described herein comprises at least one heterologous DH gene segment together with at least another DH gene segment, with which it is otherwise not natively associated (or not recombined in nature in a contiguous sequence) in a wild-type organism that does not comprise such LDH expression cassette. As a result, a recombinant (also referred to as hybrid or chimeric) DH gene construct is obtained which, after productive VDJ rearrangement, is functionally expressed within a HCDR3 sequence encoded by said heterologous DH gene segment and said at least another DH gene segment in a suitable host.

"Vectors" used herein are defined as DNA sequences that are required for the transcription of cloned recombinant nucleotide sequences, i.e., of recombinant genes and the translation of their mRNA in a suitable host organism. A vector may comprise a cassette comprising gene segments encoding specific DH genes, such as the LDH expression cassette described herein.

Plasmids and viruses and any DNA or RNA molecules may be used as a vector, whether self-replicating or not, which can be used to transform, transduce or transfect a cell. A vector may include autonomously replicating nucleotide sequences as well as genome integrating nucleotide sequences. Expression vectors may additionally comprise an origin for autonomous replication in the host cells or a genome integration site, one or more selectable markers (e.g., an amino acid synthesis gene or a gene conferring resistance to antibiotics such as puromycin, zeocin, kanamycin, G418 or hygromycin), a number of restriction enzyme cleavage sites, a suitable promoter sequence and a transcription terminator, which components are operably linked together.

A common type of vector is a "plasmid", which generally is a self-contained molecule of double-stranded DNA that can readily accept additional (foreign) DNA and which can readily be introduced into a suitable host cell. A plasmid often contains coding DNA and promoter DNA and has one or more restriction sites suitable for inserting foreign DNA. Specifically, the term "plasmid" refers to a vehicle by which a DNA or RNA sequence (e.g., a foreign gene) can be introduced into a host cell, so as to transform the host and promote expression (e.g., transcription and translation) of the introduced sequence.

The term "host cell" as used herein shall refer to primary subject cells transformed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

The term "isolated" or "isolation" as used herein with respect to a nucleic acid, an antibody or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules as described herein are also meant to include those chemically synthesized.

With reference to nucleic acids as described herein, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, such as isolated antibodies, the term "isolated" shall specifically refer to compounds that are free or substantially free of material with which they are naturally associated such as other compounds with which they are found in their natural environment, or the environment in which they are prepared (e g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy.

The term "long DH" or LDH as used herein shall mean two or more DH gene segments comprised in a DH construct, wherein at least one DH gene segment has been modified by methods described herein to include more than one DH gene segments or partial gene segments, thereby making the DH construct longer than in an wild-type animal of a certain species, or longer than average in such species (e.g., about 45 nt in humans and about 33 nt in mice). Using such LDH or DH construct, a "long HCDR3 antibody" or LHCDR3 Ab can be produced. This is specifically possible when the DH construct is utilized during VDJ rearrangement in developing B cells to form an exon to encode the VH domain of the antibody heavy chain. An LDH expression cassette described herein is still called "germline" though it contains a recombinant DH construct with at least one modified or artificial DH gene segment.

The term "Synthetic DH" or SynDH as used herein shall mean the N1-DH-N2 portion of a HCDR3 expressed by a human B lineage cell and retrieved as a cDNA sequence from the IMGT or NCBI antibody databases (see FIG. 3).

The complete HCDR3 consists of the 3' part of the VH, the DH and the 5' part of the JH as well as non-templated (N) sequences added at the 5' (N1) and 3' (N2) sides of the DH during VDJ rearrangement.

Antibodies described herein are particularly provided in the isolated form, which are substantially free of other antibodies directed against different target antigens and/or comprising a different structural arrangement of antibody domains. Still, an isolated antibody may be comprised in a combination preparation, containing a combination of the isolated antibody, e.g., with at least one other antibody, such as monoclonal antibodies or antibody fragments having different specificities.

Specifically, the antibody as described herein is provided in substantially pure form. The term "substantially pure" or "purified" as used herein shall refer to a preparation comprising at least 50% (w/w), preferably at least 60%, 70%, 80%, 90% or 95% of a compound, such as a nucleic acid molecule or an antibody. Purity is measured by methods appropriate for the compound (e.g., chromatographic methods, polyacrylamide gel electrophoresis, HPLC analysis, and the like).

The antibody as described herein may specifically be used in a pharmaceutical composition. Therefore, a pharmaceutical composition is provided which comprise an antibody as described herein and a pharmaceutically acceptable carrier or excipient. These pharmaceutical compositions can be administered in accordance with the present invention as a bolus injection or infusion or by continuous infusion. Pharmaceutical carriers suitable for facilitating such means of administration are well-known in the art.

Pharmaceutically acceptable carriers generally include any and all suitable solvents, dispersion media, coatings, isotonic and absorption delaying agents, and the like that are physiologically compatible with an immunoglobulin provided by the invention. Further examples of pharmaceutically acceptable carriers include sterile water, saline, phosphate buffered saline, dextrose, glycerol, ethanol, and the like, as well as combinations of any thereof.

Additional pharmaceutically acceptable carriers are known in the art and described in, e.g., REMINGTON'S PHARMACEUTICAL SCIENCES. Liquid formulations can be solutions, emulsions or suspensions and can include excipients such as suspending agents, solubilizers, surfactants, preservatives, and chelating agents.

Exemplary formulations as used for parenteral administration include those suitable for subcutaneous, intramuscular or intravenous injection as, for example, a solution, emulsion or suspension.

The term "therapeutically effective amount", used herein with respect to administration of a compound, e.g., an antibody as described herein, is a quantity or activity sufficient to effect beneficial or desired results, including clinical results, when administered to the subject. As such, an effective amount or synonymous quantity thereof depends upon the context in which it is being applied.

An effective amount is intended to mean that amount of a compound that is sufficient to treat, prevent or inhibit such diseases or disorder. In the context of disease, therapeutically effective amounts of the antibody as described herein are specifically used to treat, modulate, attenuate, reverse, or affect a disease or condition that benefits from the interaction of the antibody with its target antigen.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

The term "recombinant" refers to a polynucleotide or polypeptide that does not naturally occur in a host cell, or that naturally occurs in a host cell, which is modified to express a polynucleotide and produce a polypeptide in a different context or at a different level as compared to the unmodified host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "recombinant" particularly means "being prepared by or the result of genetic engineering". Alternatively, the term "engineered" is used. For example, a modified antibody or antibody domain may be modified to produce a variant by engineering the respective parent sequence to produce an engineered antibody or domain. A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host. The term "recombinant antibody", as used herein, includes immunoglobulins and in particular antibodies that are prepared, expressed, created or isolated by recombinant means, such as
  a) antibodies isolated from an animal (e.g., a non-human animal, such as a mouse) that is transgenic or transchromosomal for human immunoglobulin genes or a hybridoma prepared therefrom,
  b) antibodies isolated from a host cell transformed to express the antibody, e.g., from a transfectoma,
  c) antibodies isolated from a recombinant, combinatorial antibody library, and
  d) antibodies prepared, expressed, created or isolated by any other means that involve splicing of human immunoglobulin gene sequences to other DNA sequences. Such recombinant antibodies comprise antibodies engineered to include rearrangements and mutations which occur, for example, during antibody maturation.

"Site-specific recombination" refers to a process of recombination between two compatible recombination sites including any of the following three events:
  a) deletion of a preselected nucleic acid flanked by the recombination sites;
  b) inversion of the nucleotide sequence of a preselected nucleic acid flanked by recombination sites, and
  c) reciprocal exchange of nucleic acid regions proximate to recombination sites located on different nucleic acid molecules. It is to be understood that this reciprocal exchange of nucleic acid segments results in an integration event if one or both of the nucleic acid molecules are circular.

The term "transgene" is used herein to describe genetic material that has been or is about to be artificially inserted into the genome of a cell, and particularly a cell of a host animal. The term "transgene" as used herein refers to a nucleic acid molecule, e.g., a nucleic acid in the form of an expression construct and/or a targeting vector.

"Transgenic animal" is meant a non-human animal, usually a mammal or avian, e.g., a rodent, particularly a mouse or rat, although other mammals are envisioned, having an exogenous nucleic acid sequence present as a chromosomal or extrachromosomal element in a portion of its cells or stably integrated into its germ line DNA (i.e., in the genomic sequence of most or all of its cells).

In certain aspects of the embodiments, the transgenic animals described herein may comprise certain e.g., heterologous human immunoglobulin regions. For example, numerous methods have been developed for replacing endogenous mouse immunoglobulin regions with human immunoglobulin sequences to create partially- or fully-human antibodies for drug discovery purposes. Examples of such mice include those described in, for example, U.S. Pat Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669.

In the particularly favored aspects, the transgenic animals described herein comprise chimeric immunoglobulin segments, which are described in US 2013/0219535 by Wabl and Killeen. Such transgenic animals have a genome comprising an introduced partially human immunoglobulin region, where the introduced region comprising human variable region coding sequences and non-coding variable sequences based on the endogenous genome of the non-human vertebrate. Preferably, the transgenic cells and animals of the invention have genomes in which part or all of the endogenous immunoglobulin region is removed.

In another favored aspect, the genomic contents of animals are modified so that their B cells are capable of expressing more than one functional VH domain per cell, i.e., the cells produce bispecific antibodies, as described in WO2017035252A1.

In still another favored aspect, the genomic contents of animals are modified so that their B cells are capable of expressing Ig heavy chains without any light chains, i.e., the cell produce heavy chain only (HCO) antibodies. Such HCO antibodies are either mono- or bispecific.

The foregoing description will be more fully understood with reference to the following examples. Such examples are, however, merely representative of methods of practicing one or more embodiments of the present invention and should not be read as limiting the scope of invention.

EXAMPLES

Example 1

Method to Increase the Length of DH Gene Segments for Production of LHCDR3 Abs

An exemplary method to increase the length of the germline DH gene segments for generation of LHCDR3 Abs is illustrated in FIG. 2. (Note that the Figures and Examples contained herein are not drawn to scale.) Illustrated is a long DH (LDH) gene cassette that contains various manipulated DH gene segments that are flanked by recombination signal sequences (RSS). This cassette is inserted into the endogenous IgH locus in place of or in addition to the endogenous DH locus, as described in subsequent examples. In this example, the DH gene segments that comprise this exemplary chimeric LDH gene cassette are synthetic and of bovine (a) or human (b-d) origin and are also flanked by mouse intergenic regions to form a chimeric, ~9 kb DH vector. The endogenous human DH gene segments in the cells being targeted are also flanked by mouse intergenic regions to form a chimeric DH locus as described in US 2013/0219535. The LDH cassette depicted here is composed of the following types of DH segments as indicated on the figure. a. Bovine long IGHDS2 and DH 3.1 gene segments. Bovine antibodies with ultralong HCDR3s (50-61 aa) use IGHDS2. In this case, the IGHDS2 has been modified to encode TTVHQ (SEQ ID NO:5) amino acids at the 5' end. In bovine ultralong HCDR3s, this sequence is encoded by the 3' end of the VH gene segments and provides structural integrity to the stalk that supports the HCDR3 knob. By incorporating the sequence encoding the TTVHQ (SEQ ID NO:5) motif into the DH instead of the VH, the amount of genetic manipulations required are minimized and this modification has the potential to increase the number of VH genes that can be used in ultralong HCDR3 Abs. The bovine DH 3.1 gene segment has also been mutated to remove stop codons as described below. b. Artificial fusion germline DH gene segments (5-60 gene segments created by in silico joining of native human DH gene segments. In addition to being artificially fused, all stop codons in RF 1, 2 and 3 have been eliminated to increase the potential diversity of DH gene segments. c. Synthetic DH gene segments (SynDH, FIG. 3) corresponding to the core N1-DH-N2 portion of the HCDR3 region of LHCDR3 Abs extracted from IMGT and NCBI sequence databases. d. Modified human germline DH gene segments D2-2, D2-15 and D3-16 that are longer than the average DH and have been shown (Briney, et al., PLoS ONE, e36750, 2012) to be used by normal human B cells to produce LHCDR3 Abs. All stop codons in RF 1, 2 and 3 have been eliminated in these DH segments to increase the potential diversity of the resultant LHCDR3 antibody repertoire. This figure is an example of an LDH cassette, one of many possible LDH gene cassettes, which can vary in both the number and arrangement of the different types of DH gene segments.

Example 2

Deletion of the Endogenous DH Locus and its Replacement with the Modified LDH Gene Cassette by Recombinase-Mediated Cassette Exchange (RMCE) for the Production of LHCDR3 Abs Deletion of the endogenous heavy chain DH locus. In this example, the endogenous JH and DH gene segments are synthetic versions of their human counterparts and are flanked by mouse intergenic regions to form a chimeric DH locus as described in US 2013/0219535. Appropriate targeting sequences are inserted downstream of IGHD7-27, the most JH-proximal DH gene segment, and upstream of IGHD1-1, the most JH-distal DH gene segment by homologous recombination followed by in vitro Cre-mediated deletion of the intervening genomic region, resulting in an allele in which the DH locus is replaced by a recombinase-mediated cassette exchange (RMCE) targeting site. In this example the upstream site is targeted first, but the order can be reversed.

An exemplary method illustrating the introduction of an engineered chimeric human-mouse DH locus into the genomic locus of an ES cell is illustrated in FIGS. 4-7. In FIG. 4, a 5' homology targeting vector is provided comprising a puromycin phosphotransferase-thymidine kinase fusion protein gene (puro-TK) flanked by two different recombinase recognition sites (e.g., FRT and loxP for Flp and Cre, respectively) and two different mutant sites (e.g., modified mutant FRT (mFRT) and mutant loxP (mLoxP)) that lack the ability to recombine with their respective wild-type counterparts/sites (i.e., wild-type FRT and wild-type loxP). The targeting vector also comprises a diphtheria toxin A (DTA) gene for use in negative selection of cells containing the introduced construct in future steps. The short homology arm (SHA) is homologous to a region in the endogenous locus that is 5' of the DH locus and the long homology arm (LHA) is homologous to a contiguous region including the endogenous DH locus. The homology-targeting vector is introduced by transfection into the ES cell, which has an immunoglobulin locus comprising human VH gene segments, DH gene segments, JH gene segments that are flanked by mouse intergenic regions to form a chimeric DH locus (described in US Pub. No. 2013/0219535), and mouse immunoglobulin constant gene region genes. The ES cells are transfected by electroporation with the 5' homology-targeting vector and the puro-TK gene and flanking site-specific recombination sequences are integrated into the ES cell genome at a site 5' of the endogenous DH gene locus, resulting in the genomic structure illustrated at the bottom of the FIG. 4. The transfected cells are plated and after ~24 hours they are placed under positive selection for cells that have integrated the 5' vector into their DNA by adding puromycin to the culture media. There is also negative selection for cells that have integrated the vector into their DNA but not by homologous recombination. Non-homologous recombination will result in retention of the DTA gene, which kills cells when it is expressed, whereas the DTA gene is deleted by homologous recombination since it lies outside of the region of vector homology with the ES cell Igh locus. Colonies of drug-resistant ES cells are physically extracted from their plates after they become visible to the naked eye about a week later. These picked colonies are disaggregated, re-plated in microwell plates, and cultured for several days. Thereafter, each of the clones of cells is divided such that some of the cells can be frozen as an archive, and the rest used for isolation of DNA for analytical purposes.

DNA from the ES cell clones is screened by PCR using a widely-practiced gene-targeting assay design. For this assay, one of the PCR oligonucleotide primer sequences maps outside the region of identity shared between the 5' vector and the genomic DNA, while the other maps within the novel DNA between the two arms of genomic identity in the vector, i.e., in the puro_TK gene. According to the standard design, these assays detect pieces of DNA that would only be present in clones of ES cells derived from transfected cells that undergo fully legitimate homologous recombination between the 5' targeting vector and the endogenous mouse Igh locus. Two separate transfections are performed with the 5' vector. PCR-positive clones from the two transfections are selected for expansion followed by further analysis using Southern blot assays.

The Southern blot assays are performed according to widely used procedures using three probes and genomic DNA digested with multiple restriction enzymes chosen so that the combination of probes and digests allow the structure of the targeted locus in the clones to be identified as properly modified by homologous recombination. One of the probes maps to DNA sequence flanking the 5' side of the region of identity shared between the 5' targeting vector and the genomic DNA; a second probe maps outside the region of identity but on the 3' side; and the third probe maps within the novel DNA between the two arms of genomic identity in the vector, e.g., in the puro_TK gene. The Southern blot identifies the presence of the expected restriction enzyme-generated fragment of DNA corresponding to the correctly mutated locus, i.e., by homologous recombination with the 5' targeting vector.

Karyotypes of PCR- and Southern blot-positive clones of ES cells are analyzed using an in-situ fluorescence hybridization procedure designed to distinguish the most commonly arising chromosomal aberrations that arise in mouse ES cells. Clones with such aberrations are excluded from further use. ES cell clones that are judged to have the expected correct genomic structure based on the Southern blot data, and that also do not have detectable chromosomal aberrations based on the karyotype analysis, are selected for further use.

Acceptable clones are then modified with the 3' vector (FIG. 5) using procedures and screening assays that are essentially identical in design to those used with the 5' vector (FIG. 3) except that G418/neomycin is used instead of puromycin for selection. The PCR assays, probes and digests are also tailored to match the genomic region being modified by the 3' vector.

As illustrated in FIG. 5, the second, 3' homology targeting vector is provided comprising a neomycin resistance gene (neo); recombinase recognition sites FRT and loxP, for Flp and Cre, respectively, which have the ability to recombine with FRT and loxP sites previously integrated into the mouse genome from the first homology targeting vector (FIG. 3). The 3' homology-targeting vector also consists of a SHA that is homologous to the DH gene segments and a LHA that is homologous to a contiguous region in the endogenous ES IgH locus that includes the JH locus. A promoter sequence recognized by the RNA polymerase from the T3 bacteriophage (T3) is included in the vector downstream of JH4 to allow for rapid cloning of VDJ rearrangements from B cells, hybridomas or other sources derived from the LHCDR3 mice. The targeting vector also comprises a diphtheria toxin A (DTA) gene for use in negative selection of cells containing the introduced construct in future steps. The site-specific recombination sequences and the neomycin resistance gene of the homology-targeting vector are integrated into the ES cell genome downstream of the endogenous DH locus and the T3 promoter is integrated downstream of JH6, resulting in the genomic structure illustrated at the bottom of the FIG. 5.

Once the two recombination sites are integrated into the ES cell genome, the endogenous DH locus is then subjected to recombination deletion by introducing one of the recombinases corresponding to the sequence-specific recombination sites integrated into the genome, e.g., either Flp or Cre. Illustrated in FIG. 6 is a modified Igh locus of the ES cell genome comprising the two integrated DNA fragments. One fragment comprising mutant FRT site (mFRT), mutant LoxP site (mLoxP), puro-TK gene, wild-type FRT site, and wild-type LoxP site is integrated upstream of the DH gene locus. The other DNA fragment comprising a neomycin resistance gene (neo), wild-type FRT site and wild-type LoxP site is integrated downstream of the DH locus but upstream of the JH locus. In the presence of Flp or Cre, all the intervening sequences between the wild-type FRT or wild-type LoxP sites, including the endogenous DH locus and the neomycin resistance gene, are deleted, resulting in a genomic structure illustrated in the bottom of FIG. 6. ES cells that are resistant to puromycin but sensitive to ganciclovir are then screened for the deletion of the endogenous DH locus. The primary screening method can be carried out by Southern blotting or by polymerase chain reaction (PCR) followed by confirmation with a secondary screening technique such as Southern blotting.

FIG. 7 illustrates introduction of a site-specific targeting vector comprising the chimeric human-mouse DH gene cassette (LDH), as well as flanking mutant FRT (mFRT), mutant LoxP (mLoxP), wild-type FRT, and wild-type LoxP sites. (An exemplary version of the LDH gene cassette is shown in FIG. 2.) The Igh locus of the ES cell genome has been previously modified to delete all the DH gene segments including the intervening sequences as described in FIG. 6. As a consequence of this modification, the endogenous ES cell Igh locus is left with a puro-TK fusion gene, which is flanked by a mutant FRT site and a mutant LoxP site upstream as well as a wild-type FRT and a wild-type LoxP downstream. Upon introduction of the appropriate recombinase, the LDH gene cassette is integrated into the genome upstream of the endogenous JH locus, resulting in the genomic structure illustrated at the bottom of FIG. 7.

Primary screening procedure for the introduction of the chimeric human-mouse LDH locus is carried out by Southern blotting, or by PCR with confirmation from secondary screening methods such as Southern blotting. The screening methods are designed to detect the presence of the inserted LDH gene cassette, as described above for the other targeting constructs.

ES cell clones carrying the properly targeted LDH gene cassette in the mouse Igh locus are microinjected into mouse blastocysts from strain DBA/2 to create partially ES cell-derived chimeric mice according to standard procedures. Male chimeric mice with the highest levels of ES cell-derived contribution to their coats are selected for mating to female mice. Offspring from these matings are analyzed to confirm the presence of the LDH gene cassette. Final definitive conformation the LDH cassette has been correctly targeted and is intact and unmutated is done by DNA sequencing of the cassette and surrounding integration site. This is done by targeted locus amplification (TLA), a strategy to selectively amplify large (up to 100 kb) genomic regions on the basis of the crosslinking of physically proximal sequences (de Vree, et al., *Nature Biotechnology* 32:1019-1025 (2014) and next generation sequencing. Correctly targeted mice are used to establish a colony of mice.

Example 3

Strategy to Alter the RSS Spacer Length of the Endogenous JH Gene Segments and of the DH Gene Segments in an Introduced DH Cassette to Promote DH to DH Recombination During VDJ Rearrangement.

In the natural locus, the VH and JH gene segments have 23 bp RSS, whereas the DH gene segments are flanked on both sides by 12 bp RSS. This configuration promotes D>J and then V>DJ rearrangements and strongly inhibits D>D, as well as V>J rearrangements due to the 12/23 bp rule described above. A cassette of DH gene segments (DH-mut) with modified RSS (flanked by 23 bp RSS) is inserted between the endogenous DH and JH loci by standard techniques such as homologous recombination or RMCE in ES cells. The DH gene segment cassette consists of otherwise wild-type gene segments, the modified DH gene segments described in Example 1, or a combination thereof. The endogenous JH locus is also mutated (JH-mut) so that each JH has a 23 bp RSS. The predicted series of events during VDJ rearrangement is DH-mut>JH-mut, then DH-WT>DH-mutJH-mut, then VH>DH-WTDH-mutJH-mut. D>D fusions occur much more frequently than in wild type mice since pairs of DH gene segments are now flanked by compatible RSS, i.e., 12 and 23 bp, and thus this type of rearrangement no longer violates the 12/23 bp rule.

The invention claimed is:

1. A transgenic mouse whose genome comprises an endogenous immunoglobulin heavy chain variable region locus comprising VH and JH gene segments consisting of human variable region coding sequences and mouse non-coding sequences, and a long DH (LDH) expression cassette inserted into the endogenous immunoglobulin heavy chain variable region locus to replace all endogenous DH segments, said expression cassette comprising a recombinant DH construct comprising 5-60 different human DH gene segments wherein at least two DH gene segments are directly fused and encode at least 10 amino acids of a heavy chain CDR3 (HCDR3) amino acid sequence, wherein one fused DH gene segment comprises a human DH gene segment that is mutated to remove stop codons in reading frames (RF) 1, 2 and 3, wherein the other fused DH gene segment comprises a human DH gene segment flanked by a mouse intergenic region, and wherein the mouse is functional to express said long HCDR3 amino acid sequence with a length of at least 20 amino acids in total.

2. The transgenic mouse of claim 1, wherein the HCDR3 amino acid sequence encoded by said at least two human DH gene segments has a length ranging from 20-61 amino acids.

3. The transgenic mouse of claim 1, wherein the at least two fused DH gene segment are connected by a mouse intergenic region.

4. The transgenic mouse of claim 1, wherein the recombinant DH construct comprises an additional bovine DH gene segment.

5. The transgenic mouse of claim 1, wherein the recombinant DH construct comprises an additional bovine or human DH gene segment comprising a 12 base pair (bps) recombination signal sequence (RSS) spacer.

6. The transgenic mouse of claim 1, wherein the recombinant DH construct comprises an additional human DH gene segment comprising the deletion of one or more stop codons.

7. The transgenic mouse of claim 1, wherein the recombinant DH construct comprises an additional bovine or human DH gene segment comprising a fusion to at least one mouse intergenic region.

* * * * *

SEQUENCE LISTING

<160> NUMBER OF SEQ ID NOS: 40

<210> SEQ ID NO 1
<211> LENGTH: 39
<212> TYPE: DNA
<213> ORGANISM: Artificial Sequence
<220> FEATURE:
<223> OTHER INFORMATION: RSS

```
<400> SEQUENCE: 1
cacagtgagg ggaagtcagc gagagcccag acaaaaacc                                    39

<210> SEQ ID NO 2
<211> LENGTH: 39
<212> TYPE: DNA
<213> ORGANISM: Artificial Sequence
<220> FEATURE:
<223> OTHER INFORMATION: RSS

<400> SEQUENCE: 2
cacagtgagg ggaggtgagt gtgagcccag acaaaaacc                                    39

<210> SEQ ID NO 3
<211> LENGTH: 39
<212> TYPE: DNA
<213> ORGANISM: Artificial Sequence
<220> FEATURE:
<223> OTHER INFORMATION: RSS

<400> SEQUENCE: 3
cacagtgaca cagcccaggg cacctcctgt acaaaaacc                                    39

<210> SEQ ID NO 4
<211> LENGTH: 15
<212> TYPE: DNA
<213> ORGANISM: Artificial Sequence
<220> FEATURE:
<223> OTHER INFORMATION: DH motif

<400> SEQUENCE: 4
actactgtgc accag                                                              15

<210> SEQ ID NO 5
<211> LENGTH: 5
<212> TYPE: PRT
<213> ORGANISM: Artificial Sequence
<220> FEATURE:
<223> OTHER INFORMATION: DH motif

<400> SEQUENCE: 5

Thr Thr Val His Gln
1               5

<210> SEQ ID NO 6
<211> LENGTH: 101
<212> TYPE: DNA
<213> ORGANISM: Artificial Sequence
<220> FEATURE:
<223> OTHER INFORMATION: DH sequence

<400> SEQUENCE: 6
actactgtgc accagagttg tcctgatggt tatagttatg gttatggttg tggttatggt            60
ggttatagta gttatagtta tagttatact tacgaatata c                               101

<210> SEQ ID NO 7
<211> LENGTH: 121
<212> TYPE: DNA
<213> ORGANISM: Artificial Sequence
<220> FEATURE:
<223> OTHER INFORMATION: DH sequence

<400> SEQUENCE: 7
agactatcgg gaggatggtt actgctacac ccacagggac tcaggcccgg acatacagtc            60
```

```
ggacccgcac acaggtgtgg agctggccaa tgcatcccca ggggcactgg gctcccaagc    120
a                                                                   121

<210> SEQ ID NO 8
<211> LENGTH: 51
<212> TYPE: DNA
<213> ORGANISM: Artificial Sequence
<220> FEATURE:
<223> OTHER INFORMATION: DH sequence

<400> SEQUENCE: 8
ggtacaactg gaacgacggt atatctggaa ctacggtata tccggaacca c             51

<210> SEQ ID NO 9
<211> LENGTH: 49
<212> TYPE: DNA
<213> ORGANISM: Artificial Sequence
<220> FEATURE:
<223> OTHER INFORMATION: DH sequence

<400> SEQUENCE: 9
ggtatatctg gaacgacggt atattgggag ctactaccta tctggggac                49

<210> SEQ ID NO 10
<211> LENGTH: 52
<212> TYPE: DNA
<213> ORGANISM: Artificial Sequence
<220> FEATURE:
<223> OTHER INFORMATION: DH sequence

<400> SEQUENCE: 10
ggtatattgg gagctactac aggatattgt attattacca gctgctatgc cc            52

<210> SEQ ID NO 11
<211> LENGTH: 62
<212> TYPE: DNA
<213> ORGANISM: Artificial Sequence
<220> FEATURE:
<223> OTHER INFORMATION: DH sequence

<400> SEQUENCE: 11
aggatattgt actattggtg tatgctatac caggatattg tattggtggt atctgctact    60
cc                                                                  62

<210> SEQ ID NO 12
<211> LENGTH: 59
<212> TYPE: DNA
<213> ORGANISM: Artificial Sequence
<220> FEATURE:
<223> OTHER INFORMATION: DH sequence

<400> SEQUENCE: 12
agcatattgt ggtggggact gctattccgt attacgattt ttggagtggt tattatacc     59

<210> SEQ ID NO 13
<211> LENGTH: 68
<212> TYPE: DNA
<213> ORGANISM: Artificial Sequence
<220> FEATURE:
<223> OTHER INFORMATION: DH sequence

<400> SEQUENCE: 13
gtattacgat tacgtttggg ggagttatgc ttataccgta ttactaggat attattggtt    60
```

-continued attactac                                                                68

<210> SEQ ID NO 14
<211> LENGTH: 51
<212> TYPE: DNA
<213> ORGANISM: Artificial Sequence
<220> FEATURE:
<223> OTHER INFORMATION: DH sequence

<400> SEQUENCE: 14
ggactacagt atctacggac tacggggact acggactacg gtggtatctc c                51

<210> SEQ ID NO 15
<211> LENGTH: 63
<212> TYPE: DNA
<213> ORGANISM: Artificial Sequence
<220> FEATURE:
<223> OTHER INFORMATION: DH sequence

<400> SEQUENCE: 15
gtggatacag ctatggttac gtggatatat tggctacgat tacgtggata cagctatggt       60
tac                                                                    63

<210> SEQ ID NO 16
<211> LENGTH: 57
<212> TYPE: DNA
<213> ORGANISM: Artificial Sequence
<220> FEATURE:
<223> OTHER INFORMATION: DH sequence

<400> SEQUENCE: 16
gagtatatca gctcgtccgg gtatatcagc agctggtacg ggtatatcag cggctac          57

<210> SEQ ID NO 17
<211> LENGTH: 31
<212> TYPE: DNA
<213> ORGANISM: Artificial Sequence
<220> FEATURE:
<223> OTHER INFORMATION: DH sequence

<400> SEQUENCE: 17
aggatattgt attattacca gctgctatgc c                                      31

<210> SEQ ID NO 18
<211> LENGTH: 31
<212> TYPE: DNA
<213> ORGANISM: Artificial Sequence
<220> FEATURE:
<223> OTHER INFORMATION: DH sequence

<400> SEQUENCE: 18
aggatattgt attggtggta tctgctactc c                                      31

<210> SEQ ID NO 19
<211> LENGTH: 31
<212> TYPE: DNA
<213> ORGANISM: Artificial Sequence
<220> FEATURE:
<223> OTHER INFORMATION: DH sequence

<400> SEQUENCE: 19
gtattatcat ttttggagtg gttattatac c                                      31

<210> SEQ ID NO 20
<211> LENGTH: 36

```
<212> TYPE: DNA
<213> ORGANISM: Artificial Sequence
<220> FEATURE:
<223> OTHER INFORMATION: DH sequence

<400> SEQUENCE: 20
gtattatgtt acgtttgggg gagttatcgt tatacc                                36

<210> SEQ ID NO 21
<211> LENGTH: 33
<212> TYPE: DNA
<213> ORGANISM: Artificial Sequence
<220> FEATURE:
<223> OTHER INFORMATION: DH sequence

<400> SEQUENCE: 21
tgcattacct cggtttcggc acttactata ggg                                   33

<210> SEQ ID NO 22
<211> LENGTH: 34
<212> TYPE: DNA
<213> ORGANISM: Artificial Sequence
<220> FEATURE:
<223> OTHER INFORMATION: DH sequence

<400> SEQUENCE: 22
gtcgctggcg tagactggga gttagttctt ctgc                                  34

<210> SEQ ID NO 23
<211> LENGTH: 27
<212> TYPE: DNA
<213> ORGANISM: Artificial Sequence
<220> FEATURE:
<223> OTHER INFORMATION: DH sequence

<400> SEQUENCE: 23
tggcggacta cggtgactac ccgggag                                          27

<210> SEQ ID NO 24
<211> LENGTH: 44
<212> TYPE: DNA
<213> ORGANISM: Artificial Sequence
<220> FEATURE:
<223> OTHER INFORMATION: DH sequence

<400> SEQUENCE: 24
tggggcaccg aatctaggtg tagtggtggt agctgctact cgtc                       44

<210> SEQ ID NO 25
<211> LENGTH: 43
<212> TYPE: DNA
<213> ORGANISM: Artificial Sequence
<220> FEATURE:
<223> OTHER INFORMATION: DH sequence

<400> SEQUENCE: 25
aagatatcat gacagtagtg gttttttgcg ggactactac tat                        43

<210> SEQ ID NO 26
<211> LENGTH: 32
<212> TYPE: DNA
<213> ORGANISM: Artificial Sequence
<220> FEATURE:
<223> OTHER INFORMATION: DH sequence

<400> SEQUENCE: 26
```

```
aaattaccat atagtagtg gcaatttctc ta                              32
```

<210> SEQ ID NO 27
<211> LENGTH: 70
<212> TYPE: DNA
<213> ORGANISM: Artificial Sequence
<220> FEATURE:
<223> OTHER INFORMATION: DH sequence

<400> SEQUENCE: 27

```
tttaaggagg cgaggtggct ccggttatta ctctggtccg gggagttatt ataccaacta   60
tcggatgaat                                                         70
```

<210> SEQ ID NO 28
<211> LENGTH: 35
<212> TYPE: DNA
<213> ORGANISM: Artificial Sequence
<220> FEATURE:
<223> OTHER INFORMATION: DH sequence

<400> SEQUENCE: 28

```
ggggtcggta gcagcagctg gcgcgcacgc aggtc                          35
```

<210> SEQ ID NO 29
<211> LENGTH: 38
<212> TYPE: DNA
<213> ORGANISM: Artificial Sequence
<220> FEATURE:
<223> OTHER INFORMATION: DH sequence

<400> SEQUENCE: 29

```
ttccgcccgc cccccgtcg gggcagtggc tggtatgg                        38
```

<210> SEQ ID NO 30
<211> LENGTH: 44
<212> TYPE: DNA
<213> ORGANISM: Artificial Sequence
<220> FEATURE:
<223> OTHER INFORMATION: DH sequence

<400> SEQUENCE: 30

```
gaccccgtat tgctcgcagt ccgtggcgtt tagcagcagc tgga                44
```

<210> SEQ ID NO 31
<211> LENGTH: 32
<212> TYPE: DNA
<213> ORGANISM: Artificial Sequence
<220> FEATURE:
<223> OTHER INFORMATION: DH sequence

<400> SEQUENCE: 31

```
gggggagcgt ggtggtagct gctaccccgg gg                             32
```

<210> SEQ ID NO 32
<211> LENGTH: 32
<212> TYPE: DNA
<213> ORGANISM: Artificial Sequence
<220> FEATURE:
<223> OTHER INFORMATION: DH sequence

<400> SEQUENCE: 32

```
aagaaacgta ttacgatttt tggagtggtt ac                             32
```

<210> SEQ ID NO 33
<211> LENGTH: 39

```
<212> TYPE: DNA
<213> ORGANISM: Artificial Sequence
<220> FEATURE:
<223> OTHER INFORMATION: DH sequence

<400> SEQUENCE: 33
aggccggatt ccttggagtg gccaccccct gggggaccc                             39

<210> SEQ ID NO 34
<211> LENGTH: 59
<212> TYPE: DNA
<213> ORGANISM: Artificial Sequence
<220> FEATURE:
<223> OTHER INFORMATION: DH sequence

<400> SEQUENCE: 34
atgggggtcg atcccctggt cgggggagta gtaccagctg ctatgggaat tgtatgggg      59

<210> SEQ ID NO 35
<211> LENGTH: 51
<212> TYPE: DNA
<213> ORGANISM: Artificial Sequence
<220> FEATURE:
<223> OTHER INFORMATION: DH sequence

<400> SEQUENCE: 35
aaagtgaccc tttttggagt gattattata actttgacta ctcgtacact t              51

<210> SEQ ID NO 36
<211> LENGTH: 64
<212> TYPE: DNA
<213> ORGANISM: Artificial Sequence
<220> FEATURE:
<223> OTHER INFORMATION: DH sequence

<400> SEQUENCE: 36
tgtcctatcg ttcggggaat tattatgacg attttggttt ctcaccggag ttttactttt    60
actc                                                                  64

<210> SEQ ID NO 37
<211> LENGTH: 61
<212> TYPE: DNA
<213> ORGANISM: Artificial Sequence
<220> FEATURE:
<223> OTHER INFORMATION: DH sequence

<400> SEQUENCE: 37
gctggtgggc ccgactaccg taatgggtac aactattacg atttctatga tggttattat    60
a                                                                     61

<210> SEQ ID NO 38
<211> LENGTH: 55
<212> TYPE: DNA
<213> ORGANISM: Artificial Sequence
<220> FEATURE:
<223> OTHER INFORMATION: DH sequence

<400> SEQUENCE: 38
ggctggtggg ccaatctggc atgacgacgt caaatattac gattttaatg acggc          55

<210> SEQ ID NO 39
<211> LENGTH: 53
<212> TYPE: DNA
<213> ORGANISM: Artificial Sequence
<220> FEATURE:
```

```
<223> OTHER INFORMATION: DH sequence

<400> SEQUENCE: 39
tttggccccg actgggaaga cggtgattcc tatgatggta gtggccgggg gtt         53

<210> SEQ ID NO 40
<211> LENGTH: 58
<212> TYPE: DNA
<213> ORGANISM: Artificial Sequence
<220> FEATURE:
<223> OTHER INFORMATION: DH sequence

<400> SEQUENCE: 40
gcatatgtcg atgcagcagg tggtttcggc ggggtgggaa cgagcagacc ttgtgggc    58
```